United States Patent
Garcon et al.

(10) Patent No.: US 7,323,182 B2
(45) Date of Patent: *Jan. 29, 2008

(54) OIL IN WATER EMULSIONS CONTAINING SAPONINS

(75) Inventors: Nathalie Garcon, Wavre (BE); Patricia Marie Christine Aline Francoise Momin, Brussells (BE)

(73) Assignee: Smithkline Beecham Biologicals SG, Rixensart (BE)

( * ) Notice: Subject to any disclaimer, the term of this patent is extended or adjusted under 35 U.S.C. 154(b) by 0 days.

This patent is subject to a terminal disclaimer.

(21) Appl. No.: 10/139,815

(22) Filed: May 6, 2002

(65) Prior Publication Data

US 2003/0095974 A1    May 22, 2003

Related U.S. Application Data

(63) Continuation of application No. 09/486,997, filed as application No. PCT/EP98/05715 on Sep. 2, 1998, now abandoned.

(30) Foreign Application Priority Data

Sep. 5, 1997   (GB) .................................. 9718902.1
Oct. 2, 1997   (GB) .................................. 9720982.9

(51) Int. Cl.
*A61K 47/00*   (2006.01)

(52) U.S. Cl. .................................. 424/278.1
(58) Field of Classification Search ............. 424/184.1, 424/278.1, 283.1, 208.1, 204.1, 207.1, 230.1; 514/25, 937, 938, 943
See application file for complete search history.

(56) References Cited

U.S. PATENT DOCUMENTS 5,057,540 A *  10/1991  Kensil et al. ............ 424/278.1
5,178,862 A      1/1993  Olsen
5,585,103 A     12/1996  Raychaudhuri et al. .. 424/278.1
6,270,769 B1     8/2001  Raychaudhuri et al. .. 424/184.1
6,372,227 B1 *   4/2002  Garcon et al. ........... 424/283.1
6,623,739 B1 *   9/2003  Momin et al. ........... 424/184.1

FOREIGN PATENT DOCUMENTS

| JP | 820628 | 1/1984 |
| JP | 800605 | 6/1995 |
| WO | WO 90/01496 * | 2/1990 |
| WO | WO 90/07935 | 7/1990 |
| WO | WO 95/17120 | 6/1995 |
| WO | WO 95/17209 | 6/1995 |
| WO | WO 9517210 A1 * | 6/1995 |
| WO | WO 96/33739 | 10/1996 |
| WO | WO 9633739 A1 * | 10/1996 |
| WO | WO 97/28820 | 8/1997 |

OTHER PUBLICATIONS

Scott et al., Adjuvant activity of saponin: antigen localization studies. Int Arch Allergy Appl Immunol. 1985;77(4):409-12.*
Partial EP Search Report for PCT/EP/98/05715, 2002.
Partial EP Search Report for PCT/EP 98/05715, 2002.

* cited by examiner

*Primary Examiner*—Bruce Campell
*Assistant Examiner*—Emily M. Le
(74) *Attorney, Agent, or Firm*—Michael M. Conger

(57) ABSTRACT

The present invention relates to an oil in water emulsion vaccine composition. In particular, the present invention relates to a vaccine adjuvant formulation based on oil in water emulsion comprising a metabolisable oil and a saponin, wherein the oil and a saponin are present in a ratio of between 1:1 and 200:1. The invention further relates to methods for preparing the emulsion and its use in medicine.

22 Claims, 19 Drawing Sheets

US 7,323,182 B2

OIL IN WATER EMULSIONS CONTAINING SAPONINS

This is a continuation of application Ser. No. 09/486,997, filed Jul. 31, 2000; now abandoned which is a 371 of International Application No. PCT/EP98/05715, filed 2 Sep. 1998; which claims priority from the following Great Britain Application Nos.: GB 9718902.1, filed 5 Sep. 1997 and GB 9720982.9, filed 2 Oct. 1997.

The present invention relates to an oil in water emulsion vaccine composition. In particular, the present invention relates to a vaccine adjuvant formulation based on oil in water emulsion comprising a metabolisable oil and a saponin. The invention further relates to methods for preparing the emulsion and its use in medicine.

Induction of cytotoxic T-cell (CTL) responses occurs naturally during infection of a target cell, or uncontrolled synthesis of a tumour antigen, wherein enzymatic degradation of the target antigen takes place in the cell cytoplasm. This phenomenon allows cytoplasmic peptides derived from the pathogen, or tumour specific antigen, to enter the Th1 (endogenous antigen processing) pathway and be presented on the surface of the cell associated with an MHC class 1 molecule. If a vaccine antigen does not enter into the cytoplasm of the host cell, then it might be taken up by the cell and enter the exogenous antigen processing pathway and ultimately be presented on the surface of the cell associated with a MHC class II molecule. This alternative route generally results in T-helper responses and antigen specific antibody responses.

After conventional vaccination with subunit or non-living vaccines, antigen generally does not enter the cytoplasm of a host cell, and therefore will not enter the endogenous antigen processing pathway and ultimately will not induce a CTL response. CTL induction is believed to correlate with Th-1 cytokine profile responses, specifically with IFN-γ and IL-2 secretion. IFN-γ secretion is associated with protective responses against intracellular pathogens, including parasites, bacteria and viruses. Activation of leucocytes by IFN-γ enhances killing of intracellular pathogens and increases expression of Fc receptors. Direct cytotoxicity may also occur, especially in synergy with lymphotoxin (another product of TH1 cells). IFN-γ is also both an inducer and a product of NK cells, which are major innate effectors of protection. TH1 type responses, either through IFN-γ or other mechanisms, provide preferential help for murine IgG2a and human IgG1 immunoglobulin isotypes.

International patent application No. WO 95/17210 discloses an adjuvant emulsion system based on squalene, α-tocopherol, and polyoxyethylene sorbitan monooleate (TWEEN80), formulated with the immunostimulant QS21, optionally with 3D-MPL. This adjuvant formulation is a very potent inducer of a wide range of immune responses.

Immunologically active saponin fractions (e.g. Quil A) having adjuvant activity derived from the bark of the South American tree Quillaja Saponaria Molina are known in the art. Derivatives of Quil A, for example QS21 (an HPLC purified fraction derivative of Quil A), and the method of its production is disclosed in U.S. Pat. No. 5,057,540. Amongst QS21 (known as QA21) other fractions such as QA17 are also disclosed. The use of such saponins in isolation is accompanied with disadvantage in that local necrosis, that is to say, localised tissue death, occurs at the injection site, thereby leading to pain.

Immunologically active saponin fractions having adjuvant activity derived from the bark of the South American tree Quillaja Saponaria Molina are known in the art. For example, QS21, an HPLC purified fraction from the Quillaja Saponaria Molina tree, and the method of its production (known as QA21) is disclosed in U.S. Pat. No. 5,057,540. The use of such saponins is accompanied with a disadvantage in that local necrosis, that is to say, localised tissue death, occurs at the injection site, which leads to pain.

3 De-O-acylated monophosphoryl lipid A is a well known adjuvant manufactured by Ribi Immunochem, Montana. Chemically it is often supplied as a mixture of 3 De-O-acylated monophosphoryl lipid A with either 4, 5, or 6 acylated chains. It can be prepared by the methods taught in GB 2122204B. A preferred form of 3 De-O-acylated monophosphoryl lipid A is in in the form of an emulsion having a small particle size less than 0.2 μm in diameter, and its method of manufacture is disclosed in European Patent No. EP 0671 948 B1.

In order for any oil in water composition to be suitable for human administration, the oil phase of the emulsion system has to comprise a metabolisable oil. The meaning of the term metabolisable oil is well known in the art. Metabolisable can be defined as "being capable of being transformed by metabolism" (Dorland's Illustrated Medical Dictionary, W. B. Sanders Company, 25th edition (1974)). The oil may be any vegetable oil, fish oil, animal oil or synthetic oil, which is not toxic to the recipient and is capable of being transformed by metabolism. Nuts, seeds, and grains are common sources of vegetable oils. Synthetic oils are also part of this invention and can include commercially available oils such as NEOBEE® and others. Squalene (2,6,10,15,19,23-Hexamethyl-2,6,10,14,18,22-tetracosahexaene) is an unsaturated oil which is found in large quantities in shark-liver oil, and in lower quantities in olive oil, wheat germ oil, rice bran oil, and yeast, and is a particularly preferred oil for use in this invention. Squalene is a metabolisable oil virtue of the fact that it is an intermediate in the biosynthesis of cholesterol (Merck index, 10th Edition, entry no.8619).

Oil in water emulsions per se are well known in the art, and have been suggested to be useful as adjuvant compositions (EPO 399843).

The immunological responses to administration of antigen formulated in the oil in water emulsions described in International patent application No.WO 95/17210, can be characterised in that both Th2 and Th1 responses are observed. Given that for in many cases Th1-type responses have been identified as critical for the prophylaxis and treatment of disease, it is, therefore, desirable that a more Th1 biased adjuvant is developed. This has most surprisingly been achieved by the present inventors not by addition of extra immunostimulators, but by a reduction of one of the original components.

The oil in water adjuvant emulsions described in International patent application No.WO 95/17210 have a high ratio of squalene: saponin (w/w) of 240:1. The embodiments of the present invention have the ratio of squalene:QS21 in the range of 1:1 to 200:1, also preferred is the range 20:1 to 200:1, preferably 20:1 to 100:1, and most preferably substantially 48:1. This reduction of one of the components has the surprising effect of qualitatively improving the resultant immune response. Using this novel adjuvant formulation strong Th2-type responses are maintained, but moreover such formulations elicit an enhanced immune response specifically associated with Th1-type responses, characterised by high IFN-γ, T-cell proliferative and CTL responses.

One preferred embodiment of the present invention is an adjuvant or pharmaceutical formulation comprising QuilA or derivative thereof, such as QS21 and an oil in water emulsion, wherein the oil in water emulsion comprises a metabolisible oil, such as squalene, and a polysorbate (including polyoxyethylene sorbitan monooleate, TWEEN 80™), said emulsions being characterised in that the ratio of the oil:QS21 is in the range of 20:1 to 200:1 (w/w). In another preferred embodiment, the adjuvant formulation further comprises other immunomodulators, including α-tocopherol and 3D-MPL.

Such formulations once combined with an antigen or antigenic preparation is suitable for a broad range of monovalent or polyvalent vaccines. Additionally the oil in water emulsion may contain polyoxyethylene sorbitan trioleate (SPAN 85). A preferred form of 3 De-O-acylated monophosphoryl lipid A is disclosed in International patent application published under No. 92116556—SmithKline Beecham Biologicals s.a.

Preferably the vaccine formulations of the present invention contain an antigen or antigenic composition capable of eliciting an immune response against a human pathogen, which antigen or antigenic composition is derived from HIV-1, (such as tat, nef, gp120 or gp160), human herpes viruses, such as gD or derivatives thereof or Immediate Early protein such as ICP27 from HSV1 or HSV2, cytomegalovirus ((esp Human)(such as gB or derivatives thereof), Rotavirus (including live-attenuated viruses), Epstein Barr virus (such as gp350 or derivatives thereof), Varicella Zoster Virus (such as gpI, II and IE63), or from a hepatitis virus such as hepatitis B virus (for example Hepatitis B Surface antigen or a derivative thereof), hepatitis A virus, hepatitis C virus and hepatitis E virus, or from other viral pathogens, such as paramyxoviruses: Respiratory Syncytial virus (such as F and G proteins or derivatives thereof), parainfluenza virus, measles virus, mumps virus, human papilloma viruses (for example HPV6, 11, 16, 18,), flaviviruses (e.g. Yellow Fever Virus, Dengue Virus, Tick-borne encephalitis virus, Japanese Encephalitis Virus) or Influenza virus, or derived from bacterial pathogens such as *Neisseria* spp, including *N. gonorrhea* and *N. meningitidis* (for example capsular polysaccharides and conjugates thereof, transferrin-binding proteins, lactoferrin binding proteins, PilC, adhesins); *Streptococcus* spp, including *S. pneumoniae* (for example capsular polysaccharides and conjugates thereof, PsaA, PspA, streptolysin, choline-binding proteins), *S. pyogenes* (for example M proteins or fragments thereof, C5A protease, lipoteichoic acids), *S. agalactiae, S. mutans; Haemophilus* spp, including *H. influenzae* type B (for example PRP and conjugates thereof), non typeable *H. influenzae* (for example OMP26, high molecular weight adhesins, P5, P6, lipoprotein D), *H. ducreyi; Moraxella* spp, including *M catarrhalis*, also known as *Branhamella catarrhalis* (for example high and low molecular weight adhesins and invasins); *Bordetella* spp, including *B. pertussis* (for example pertactin, pertussis toxin or derivatives thereof, filamenteous hemagglutinin, adenylate cyclase, fimbriae), *B. parapertussis* and *B. bronchiseptica; Mycobacterium* spp., including *M. tuberculosis* (for example ESAT6, Antigen 85A, -B or —C), *M. bovis, M. leprae, M. avium, M. paratuberculosis, M. smegmatis; Legionella* spp, including *L. pneumophila; Escherichia* spp, including enterotoxic *E. coli* (for example colonization factors, heat-labile toxin or derivatives thereof, heat-stable toxin or derivatives thereof), enterohemorragic *E. coli*, enteropathogenic *E. coli* (for example shiga toxin-like toxin or derivatives thereof); *Vibrio* spp including *V. cholera* (for example cholera toxin or derivatives thereof; *Shigella* spp, including *S. sonnei, S. dysenteriae, S. flexnerii; Yersinia* spp, including *Y. enterocolitica* (for example a Yop protein), *Y. pestis, Y. pseudotuberculosis; Campylobacter* spp, including *C. jejuni* (for example toxins, adhesins and invasins) and *C. coli; Salmonella* spp, including *S. typhi, S. paratyphi, S. choleraesuis, S. enteritidis; Listeria* spp., including *L. monocytogenes; Helicobacter* spp, including *H. pylori* (for example urease, catalase, vacuolating toxin); *Pseudomonas* spp, including *P. aeruginosa; Staphylococcus* spp., including *S. aureus, S. epidermidis; Enterococcus* spp., including *E. faecalis, E. faecium; Clostridium* spp., including *C. tetani* (for example tetanus toxin and derivative thereof), *C. botulinum* (for example botulinum toxin and derivative thereof), *C. difficile* (for example clostridium toxins A or B and derivatives thereof); Bacillus spp., including *B. anthracis* (for example botulinum toxin and derivatives thereof; Corynebacterium spp., including *C. diphtheriae* (for example diphtheria toxin and derivatives thereof); Borrelia spp., including *B. burgdorferi* (for example OspA, OspC, DbpA, DbpB), *B. garinii* (for example OspA, OspC, DbpA, DbpB), *B. afzelii* (for example OspA, OspC, DbpA, DbpB), *B. andersonii* (for example OspA, OspC, DbpA, DbpB), *B. hermsii;* Ehrlichia spp., including *E. equi* and the agent of the Human Granulocytic Ehrlichiosis; *Rickettsia* spp, including *R. rickettsii;* Chiamydia spp., including *C. trachomatis* (for example MOMP, heparin-binding proteins), *C. pneumoniae* (for example MOMP, heparin-binding proteins), *C. psittaci;* Leptospira spp., including *L. interrogans; Treponema* spp., including *T. pallidum* (for example the rare outer membrane proteins), *T. denticola, T. hyodysenteriae;* or derived from parasites such as *Plasmodium* spp., including *P. falciparum;* Toxoplasma spp., including *T. gondii* (for example SAG2, S&G3, Tg34); Entamoeba spp., including *E. histolytica;* Babesia spp., including *B. microti; Trypanosoma* spp., including *T. cruzi; Giardia* spp., including *G. lamblia;* Leshmania spp., including *L. major;* Pneumocystis spp., including *P. carinii; Trichomonas* spp., including *T. vaginalis;* Schisostoma spp., including *S. mansoni,* or derived from yeast such as Candida spp., including *C. albicans; Cryptococcus* spp., including *C. neoformans.*

Derivatives of Hepatitis B Surface antigen are well known in the art and include, inter alia, those PreS1, PreS2 S antigens set forth described in European Patent applications EP-A-414 374; EP-A-0304 578, and EP 198-474. In one preferred aspect the vaccine formulation of the invention comprises the HIV-1 antigen, gp120, especially when expressed in CHO cells. In a further embodiment, the vaccine formulation of the invention comprises gD2t as hereinabove defined.

In a preferred embodiment of the present invention vaccines containing the claimed adjuvant comprise the HPV viruses considered to be responsible for genital warts, (HPV 6 or HPV 11 and others), and the HPV viruses responsible for cervical cancer (HPV16, HPV18 and others). Particularly preferred forms of vaccine comprise L1 particles or capsomers, and fusion proteins comprising one or more antigens selected from the HPV 6 and HPV 11 proteins E6, E7, L1, and L2. The most preferred forms of fusion protein are: L2E7 as disclosed in GB 95 15478.7, and proteinD(⅓)-E7 disclosed in GB 9717953.5.

Vaccines of the present invention further comprise antigens derived from parasites that cause Malaria. For example, preferred antigens from *Plasmodia falciparum* include RTS,S and TRAP.RTS is a hybrid protein comprising substantially all the C-terminal portion of the circumsporozoite (CS) protein of *P. falciparum* linked via four amino acids of the preS2 portion of Hepatitis B surface antigen to the surface (S) antigen of hepatitis B virus. It's full structure is disclosed in the International Patent Application No. PCT/EP92/02591, published under Number WO 93/10152 claiming priority from UK patent application No. 9124390.7. When expressed in yeast RTS is produced as a lipoprotein particle, and when it is co-expressed with the S antigen from HBV it produces a mixed particle known as RTS,S. TRAP antigens are described in the International Patent Application No. PCT/GB89/00895, published under WO 90/01496. A preferred embodiment of the present invention is a Malaria vaccine wherein the antigenic preparation comprises a combination of the RTS,S and TRAP antigens. Other plasmodia antigens that are likely candidates to be components of a multistage Malaria vaccine are *P. faciparum* MSP1, AMA1, MSP3, EBA, GLURP, RAP1, RAP2, Sequestrin, PfEMP1, Pf332, LSA1, LSA3, STARP, SALSA, PfEXP1, Pfs25, Pfs28, PFS27/25, Pfs16, Pfs48/45, Pfs230 and their analogues in Plasmodium spp.

The formulations may also contain an anti-tumour antigen and be useful for the immunotherapeutic treatment cancers. For example, the adjuvant formulation finds utility with tumour rejection antigens such as those for prostrate, breast, colorectal, lung, pancreatic, renal or melanoma cancers. Exemplary antigens include MAGE 1 and MAGE 3 or other MAGE antigens for the treatment of melanoma, PRAME, BAGE or GAGE (Robbins and Kawakami, 1996, Current Opinions in Immunology 8, pps 628-636; Van den Eynde et al., International Journal of Clinical & Laboratory Research (submitted 1997); Correale et al. (1997), Journal of the National Cancer Institute 89, p293. Indeed these antigens are expressed in a wide range of tumour types such as melanoma, lung carcinoma, sarcoma and bladder carcinoma. Other Tumor-Specific antigens are suitable for use with adjuvant of the present invention and include, but are not restricted to Prostate specific antigen (PSA) or Her-2/neu, KSA (GA733), MUC-1 and carcinoembryonic antigen (CEA). Accordingly in one aspect of the present invention there is provided a vaccine comprising an adjuvant composition according to the invention and a tumour rejection antigen.

It is foreseen that compositions of the present invention will be used to formulate vaccines containing antigens derived from Borrelia sp. For example, antigens may include nucleic acid, pathogen derived antigen or antigenic preparations, recombinantly produced protein or peptides, and chimeric fusion proteins. In particular the antigen is OspA. The OspA may be a full mature protein in a lipidated form virtue of the host cell (*E. Coli*) termed (Lipo-OspA) or a non-lipidated derivative. Such non-lipidated derivatives include the non-lipidated NS1-OspA fusion protein which has the first 81 N-terminal amino acids of the non-structural protein (NS 1) of the influenza virus, and the complete OspA protein, and another, MDP-OspA is a non-lipidated form of OspA carrying 3 additional N-terminal amino acids.

Vaccines of the present invention may be used for the prophylaxis or therapy of allergy. Such vaccines would comprise allergen specific (for example Der p1) and allergen non-specific antigens (for example the stanworth decapeptide).

The ratio of QS21:3D-MPL (w/w) in a preferred embodiment of the present invention will typically be in the order of 1:10 to 10:1; preferably 1:5 to 5:1 and often substantially 1:1. The preferred range for optimal synergy is from 2.5:1 to 1:13D MPL:QS21. Typically, the dosages of QS21 and 3D-MPL in a vaccine for human administration will be in the range 1 μg-1000 μg, preferably 10 μg-500 μg, and most preferably 10-100 μg per dose. Typically the oil in water will comprise from 2 to 10% squalene, from 2 to 10% α-tocopherol and from 0.4 to 2% polyoxyethylene sorbitan monooleate (TWEEN 80). Preferably the ratio of squalene: α-tocopherol is equal or less than 1 as this provides a more stable emulsion. Polyoxyethylene sorbitan trioleate (SPAN 85) may also be present at a level of 0.5-1%. In some cases it may be advantageous that the vaccines of the present invention will further contain a stabiliser, for example other emulsifiers/surfactants, including caprylic acid (merck index 10th Edition, entry no. 1739), of which Tricaprylin is a particularly preferred embodiment.

Therefore, another embodiment of this invention is a vaccine containing QS21 and an oil in water emulsion falling within the desired ratio, which is formulated in the presence of a sterol, preferably cholesterol, in order to reduce the local reactogenicity conferred by the QS21. The ratio of the QS21 to cholesterol (w/w), present in a specific embodiment of the present invention, is envisaged to be in the range of 1:1 to 1:20, substantially 1:10.

The previous emulsions used in International patent application No. WO 95/17210 obviously holds some advantages over conventional non-Th1 inducing adjuvants.

However, the inclusion of QS21 has so far made this potent adjuvant reactogenic, thereby, leading to pain. It has been observed that formulation of the QS21 into cholesterol containing liposomes may help prevent the necrosis occurring at the site of injection. This observation is subject to the International Patent Application No. PCT/EP96/01464.

In embodiments of the present invention the preferred sterol is cholesterol. Other sterols which could be used in embodiments of the present invention include β-sitosterol, stigmasterol, ergosterol, ergocalciferol and cholesterol. Sterols are well known in the art. Cholesterol is well known and is, for example, disclosed in the Merck Index, 11th Edn., page 341, as a naturally occurring sterol found in animal fat.

QS21 in aqueous solution is known to degenerate over time into an adjuvant-inactive form, QS21-H, which degeneration is mediated by OH hydrolysis by the aqueous medium. Such degeneration may occur when the QS21 is present in the aqueous phase of an oil in water adjuvant. Surprisingly it has been found that the addition of cholesterol to the oil phase of the oil in water emulsion has the effect of maintaining the QS21 in its active form, with obvious benefits to the shelf-life of the adjuvant/vaccine formulation. The present invention provides a method of stabilising a preparation of a saponin, preferably QS21, in its non-hydrolysed adjuvant-active form, when the QS21 is present in an oil in water emulsion based adjuvant. This method comprises the addition of a sterol, preferably cholesterol, into the oil phase of an oil in water emulsion.

Such preparations are used as vaccine adjuvant systems and once formulated together with antigen or antigenic preparations for potent vaccines. Advantageously they preferentially induce a Th1 response.

The emulsion systems of the present invention have a small oil droplet size in the sub-micron range. Preferably the oil droplet sizes will be in the range 120 to 750 nm, and most preferably from 120-600 nm in diameter.

The amount of protein in each vaccine dose is selected as an amount which induces an immunoprotective response without significant, adverse side effects in typical vaccinees. Such amount will vary depending upon which specific immunogen is employed and how it is presented. Generally, it is expected that each dose will comprise 1-1000 μg of protein, preferably 1-500 μg, preferably 1-100 μg, most preferably 1 to 50 μg. An optimal amount for a particular vaccine can be ascertained by standard studies involving observation of appropriate immune responses in subjects. Following an initial vaccination, subjects may receive one or several booster immunisation adequately spaced.

The formulations of the present invention maybe used for both prophylactic and therapeutic purposes. In a further aspect of the present invention there is provided a vaccine as herein described for use in medicine. Vaccine preparation is generally described in New Trends and Developments in Vaccines, edited by Voller et al., University Park Press, Baltimore, Md., U.S.A. 1978.

It is foreseen that compositions of the present invention will be used to formulate vaccines containing antigens derived from a wide variety of sources. For example, antigens may include human, bacterial, or viral nucleic acid, pathogen derived antigen or antigenic preparations, tumour derived antigen or antigenic preparations, host-derived antigens, including the histamine releasing decapeptide of IgE (known as the Stanworth decapeptide), recombinantly produced protein or peptides, and chimeric fusion proteins.

The vaccine preparations of the present invention may be used to protect or treat a mammal susceptible to, or suffering from a disease, by means of administering said vaccine via systemic or mucosal route. These administrations may include injection via the intramuscular, intraperitoneal, intradermal or subcutaneous routes; or via mucosal administration to the oral/alimentary, or respiratory tracts.

EXAMPLE 1

Figure 1:
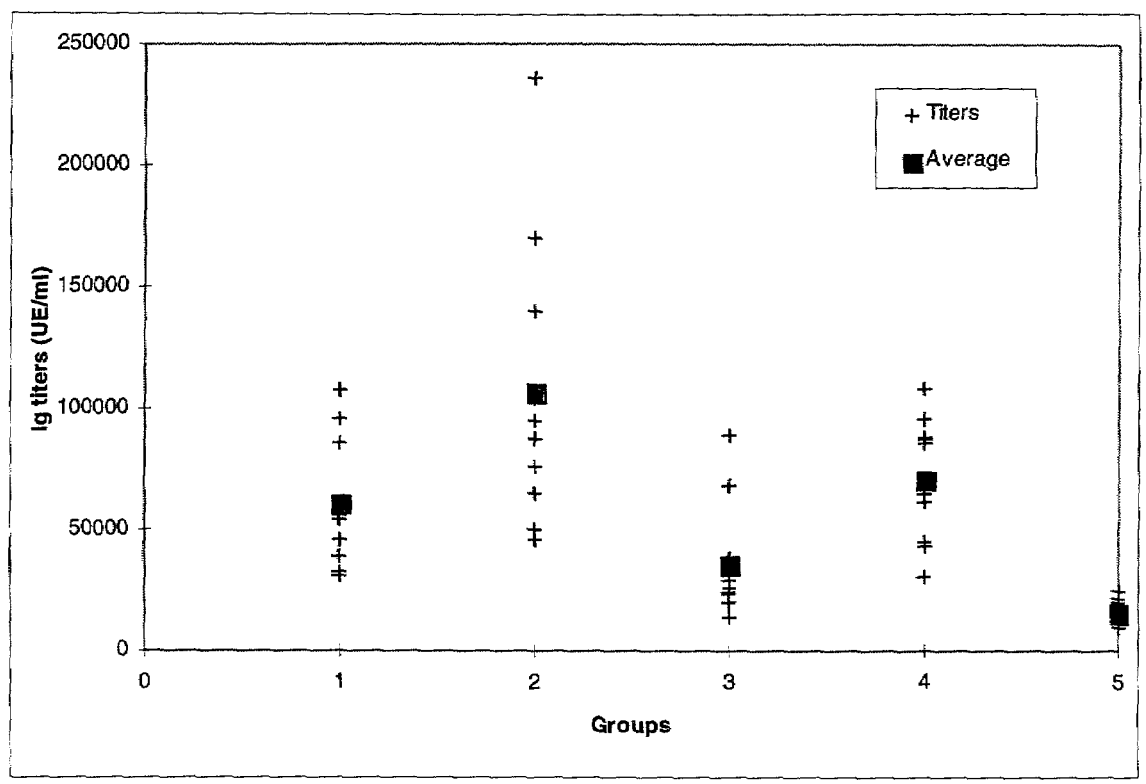
FIG. 1, Shows Hbs specific Ig antibody responses measured on both individual mouse sera, and group average, 14 days post IL.

Preparation of the Oil in Water Emulsion Adjuvants

The oil in water emulsion adjuvant formulations used in the subsequent examples were each made comprising the following oil in water emulsion component: 5% Squalene, 5% α-tocopherol, 2.0% polyoxyethylene sorbitan monooleate (TWEEN 80).

The emulsion was prepared as follows as a 2 fold concentrate. All examples used in the immunological experiments are diluted with the addition of extra components and diluents to give either a 1× concentration (equating to a squalene:QS21 ratio (w/w) of 240:1) or faker dilutions thereof.

Briefly, the TWEEN 80 is dissolved in phosphate buffered saline (PBS) to give a 2% solution in the PBS. To provide 100 ml of a two fold concentrate emulsion, 5 ml of DL alpha tocopherol and 5 ml of squalene are vortexed to mix thoroughly. 95 ml of PBS/TWEEN solution is added to the oil and mixed thoroughly. The resulting emulsion is then passed through a syringe needle and finally microfluidised by using an M110S Microfluidics machine. The resulting oil droplets have a size of approximately 145-180 nm (expressed as z av. measured by PCS) and is termed "full dose" SB62.

The other adjuvant/vaccine components (QS21, 3D-MPL or antigen) are added to the emulsion in simple admixture.

The antigen containing vaccines used herein are formulated either with full dose SB62 adjuvant to give a high squalene:QS21 ratio (240:1) or with a lower amount of SB62 to give a low ratio formulation (48:1), these adjuvant formulations are called SB62 and SB62' respectively. Other vaccines may optionally be formulated with the addition of cholesterol to the oil phase of the emulsion (denoted by the addition of the letter "c").

EXAMPLE 2

Immunogenicity Studies with Recombinant Antigen S.L*

A study was conducted in Balb/C mice in order to compare the immunogenicity of various S,L* containing formulations. S,L* is a composite antigen comprising a modified surface antigen L protein (L*) and an S-protein both derived from the Hepatitis B virus (HB. This composite antigen is the subject of European Patent application No. EP 0 414 374. This immunisation scheme used in the HBs transgenic mouse mouse model which has been shown previously to support the induction of CTL in Balb/c mice.

Different adjuvant formulations, using the emulsion systems as described in example 1, with differing ratios of squalene:QS21, and optionally comprising cholesterol (QS21 cholesterol ratio w/w of 1:10), were combined with S,L* and compared in their ability to induce humoral and cell mediated immune responses (cytokine production and CTL). S,L* adsorbed onto Aluminium hydroxide (AlOH$_3$) was used as a Th2 inducing control.

Briefly, groups of 10 mice were immunised intramuscularly 4 times at 3 weeks interval with 2 µg lyophilised S,L* combined with various oil in water emulsion systems (SB62). 14 days following the fourth immunisation the production of cytokines (IL5 and IFN-γ) and CTL activity was analysed after in vitro restimulation of spleen and lymph nodes cells with S,L* antigen. Antibody response to S,L* and the isotypic profile induced were monitored by ELISA at 21 days post II and 14 days post IV.

Groups of Mice

Groups of 10 Balb/C mice were immunised intramuscularly with formulations described below. SB62 was formulated together with the antigen at a high (240:1, SB62) or low (48:1, SB62') ratio of squalene:QS21, optionally with the addition of cholesterol (c).

TABLE 1

Groups of mice and vaccines compositions used in example 2.

| Group | Antigen S,L* | Adjuvant name | Composition of adjuvant formulation |
|---|---|---|---|
| GR 1 | 2 µg | SB62 | 25 µl SB62/5 µg QS21/5 µg 3D-MPL |
| GR 2 | 2 µg | SB62c | 25 µl SB62c/5 µg QS21/5 µg 3D-MPL |
| GR 3 | 2 µg | SB62' | 5 µl SB62/ 5 µg QS21/5 µg 3D-MPL |
| GR 4 | 2 µg | SB62'c | 5 µl SB62c/5 µg QS21/5 µg 3D-MPL |
| GR 5 | 2 µg | Alum | 50 µg AlOH$_3$ |

Immunisatign Scheme:

Animals were immunised intramuscularly in the leg (50 µl for all groups except for group 5 where 100 µl was injected) at days 0, 21, 42 and 63. Blood was taken from the retroorbital sinus at various time points post immunisations. On day 77, animals from each group were sacrificed, spleens and lymph nodes draining the site of injection (iliac lymph nodes) were taken out for in vitro restimulation. Pools of 3 or 4 spleens and 1 pool of 10 LN were obtained for each group and treated separately in the in vitro assays.

Mouse Serology

Quantitation of anti-HBs antibody was performed by Elisa using HB surface antigen as coating antigen. Antigen and antibody solutions were used at 50 µl per well. Antigen was diluted at a final concentration of 1 µg/ml in PBS and was adsorbed overnight at 4° C. to the wells of 96 wells microtiter plates (Maxisorb Immuno-plate, Nunc, Denmark). The plates were then incubated for 1 hr at 37° C. with PBS containing 1% bovine serum albumin and 0.1% TWEEN 20 (saturation buffer). Two-fold dilutions of sera (starting at 1/100 dilution) in the saturation buffer were added to the HBs-coated plates and incubated for 1 hr 30 min at 37° C. The plates were washed four times with PBS 0.1% TWEEN 20 and biotin-conjugated anti-mouse IgG1, IgG2a, IgG2b or Ig (Amersham, UK) diluted 1/1000 in saturation buffer was added to each well and incubated for 1 hr 30 min at 37° C. After a washing step, streptavidin-biotinylated peroxydase complex (Amersham, UK) diluted 1/5000 in saturation buffer was added for an additional 30 min at 37° C. Plates were washed as above and incubated for 20 min with a solution of o-phenylenediamine (Sigma) 0.04% H$_2$O$_2$ 0.03% in 0.1% TWEEN 200.05M citrate buffer pH4.5. The reaction was stopped with H$_2$SO$_4$ 2N and read at $^{492}/_{620}$ nm. ELISA titers were calculated from a reference by Softmax-Pro (using a four parameters equation) and expressed in EU/ml.

T Cell Proliferation 2 weeks after the second immnunisation, mice were killed, spleen and lymph nodes were removed aseptically in pools (3 or 4 organs per pool for splenic cells, 1 pool of 10 organs for LNC). Cell suspensions were prepared in RPMI 1640 medium (GIBCO) containing 2 mM L-glutamine, antibiotics, 5×10$^{-5}$ M 2-mercaptoedmaol, and 1% syngeneic normal mouse serum. Cells were cultured at a final concentration of 2×10$^6$ cells/ml (for LNC or SPC) in 200 µl in round-bottomed 96 well-plates with different concentrations (10-0.03 µg/ml) of S,L* antigen (25D84). Each test was carried out in quadriplicate. After 96 hr of culture at 37° C. under 5% CO2, the cells were pulsed for 18 hr with 3H-Thymidine (Amersham, UK, 5Ci/mmol) at 0.5 µCi/well and then harvested on fibre glass filters with a cell harvester. Incorporated radioactivity was measured in a liquid scintillation counter. Results are expressed in cpm (mean cpm in quadriplicate wells) or as stimulation indices (mean cpm in cultures of cells with antigen/mean cpm in cultures of cells without antigen).

Cytokine Production 2 weeks after the second immunisation, mice were killed, spleen and lymph nodes were removed aseptically in pools (3 or 4 organs per pool for splenic cells, 1 pool of 10 organs for LNC). Cell suspensions were prepared in RPMI 1640 medium (GIBCO) containing 2 mM L-glutamine, antibiotics, 5×10$^{-5}$ M 2-mercaptoethanol, and 5% foetal calf serum. Cells were cultured at a final concentration of 2.5 to 5×10$^6$ cells/ml (respectively for LNC or SPC) in 1 ml, in flat-bottomed 24 well—with different concentrations (1-0.01 µg/ml) of S,L* (25D84). Supernatants were harvested 96 hrs later and frozen until tested for the presence of IFNg and IL-5 by Elisa.

IFN-γ Production

Quantitation of IFNγ was performed by Elisa using reagents from Genzyme. Samples and antibody solutions were used at 50 µl per well. 96-well microtiter plates (Maxisorb Immuno-plate, Nunc, Denmark) were coated overnight at 4° C. with 50 µl of hamster anti-mouse IFNg diluted at 1.5 µg/ml in carbonate buffer pH9.5. Plates were then incubated for 1 hr at 37° C. with 100 µl of PBS containing 1% bovine serum albumin and 0.1% TWEEN 20 (saturation buffer). Two-fold dilutions of supernatant from in vitro stimulation (starting at ½) in saturation buffer were added to the anti-IFNg-coated plates and incubated for 1 hr 30 at 37° C. The plates were washed 4 times with PBS TWEEN 0.1% (wash buffer) and biotin-conjugated goat anti-mouse IFNg diluted in saturation buffer at a final concentration of 0.5 µg/ml was added to each well and incubated for 1 hr at 37° C. After a washing step, AMDEX conjugate (Amersham) diluted 1/10000 in saturation buffer was added for 30 min at 37° C. Plates were washed as above and incubated with 50 µl of TMB (Biorad) for 10 min. The reaction was stopped with H$_2$SO$_4$ 0.4N and read at 450 nm. Concentrations were calculated using a standard curve (mouse IFNγ standard) by SoftmaxPro (four parameters equation) and expressed in pg/ml.

IL-5 Production

Quantitation of IL5 was performed by Elisa using reagents from Pharmingen. Samples and antibody solutions were used at 50 µl per well. 96-well microtiter plates (Maxisorb Immuno-plate, Nunc, Denmark) were coated overnight at 4° C. with 50 µl of rat anti-mouse IL5 diluted at 1 µg/m in carbonate buffer pH 9.5. Plates were then incubated for 1 hr at 37° C. with 100 µl PBS containing 1% bovine serum albumin and 0.1% TWEEN 20 (saturation buffer)Two-fold dilutions of supernatant from in vitro stimulation (starting at ½) in saturation buffer were added to the anti-IL5s-coated plates and incubated for 1 hr 30 at 37° C. The plates were washed 4 times with PBS TWEEN 0.1% (wash buffer) and biotin-conjugated rat anti-mouse IL5 diluted in saturation buffer at a final concentration of 1 µg/ml was added to each well and incubated for 1 hr at 37°. After a washing step, AMDEX conjugate (Amersham) diluted $1/10000$ in saturation buffer was added for 30 min at 37° C. Plates were washed as above and incubated with 50 µl of TMB (Biorad) for 15 min. The reaction was stopped with $H_2SO_4$ 0.4N and read at 450 nm. Concentrations were calculated using a standard curve (recombinant mouse IL5) by SoftmaxPro (four parameters equation) and expressed in pg/ml.

CTL Induction 2 weeks after the second imimunisation, mice were killed, spleens were removed aseptically in pools of 3 or 4 mice (2 pools of 3 and one pool of 4 mice per group). Cell suspensions were prepared in RPMI 1640 medium (GIBCO) containing 2 MM L-glutamine, antibiotics, $5 \times 10^{-5}$ M 2-mercaptoethanol, and 5% foetal calf serum. Cells were cultured at a final concentration of $2 \times 10^6$ cells/ml in 10 ml medium containing 2 µg/ml SL* and 1.25% ConA sup (25 $cm^2$ Falcon flasks) and incubated for 8 days at 37° C. under 5% $CO_2$.

CTL Assay

The day before the CTL assay (d7), target cells were prepared by incubation of P815 cells ($10^6$ cells/ml) with S,L* (batch 25D84) or peptide $S_{28-39}$ at 10 µg/ml. Following 1 hr incubation in 15 ml Falcon tubes in a small volume, cells are transferred to 24 well plates and incubated ON at 37° C.

The day of the assay, $2 \times 10^6$ S,L* and $S_{28-39}$ pulsed P815 cells and P815-S are centrifugated, resuspended in 50 µl FCS and incubated with 75 µl $^{51}$Cr (375 µCi) for 1 hr at 37° C. (shaking every 15'). Cells are then washed 4 times with 10 ml complete medium and incubated for 30' at 4° C. following the 4th wash. Cells are then centrifugated and resuspended at a concentration of $2 \times 10^4$ cells/ml.

Effector cells are then centrifugated, counted and resuspended at $2 \times 10^6$ cells/ml. Three fold serial dilutions of effector cells are done in 96 V-bottomed plates, starting at a concentration of $2 \times 10^5$ cells/well/100 µl.

$2 \times 10^3$ target cells in 100 µl are added to effector cells in triplicate. Spontaneous and maximum release are assessed by incubating target cells respectively with medium or Triton X100 3%.

Plates are centrifuigated 3' at 700 rpm and incubated for 4 hrs at 37° C. Following the incubation time, 50 µl of supernatant is transferred from each well to Luma-plates and dried overnight before counting in Top-count scintillation counter.

Results are expressed as specific lysis and calculated as follow:

% $SR$=(mean cpm sample−mean cpm medium/mean cpm max−mean cpm medium)×100

Results

Serology

Humoral responses (Ig and IgG isotypes) were measured by ELISA using HB surface antigen as coating antigen. Only data from the 21 days post II time point are shown. These results are given in FIGS. 1 and 2.

FIG. 1, Shows Hbs specific Ig antibody responses measured on both individual mouse sera, and group average, 14 days post II.

Figure 2:
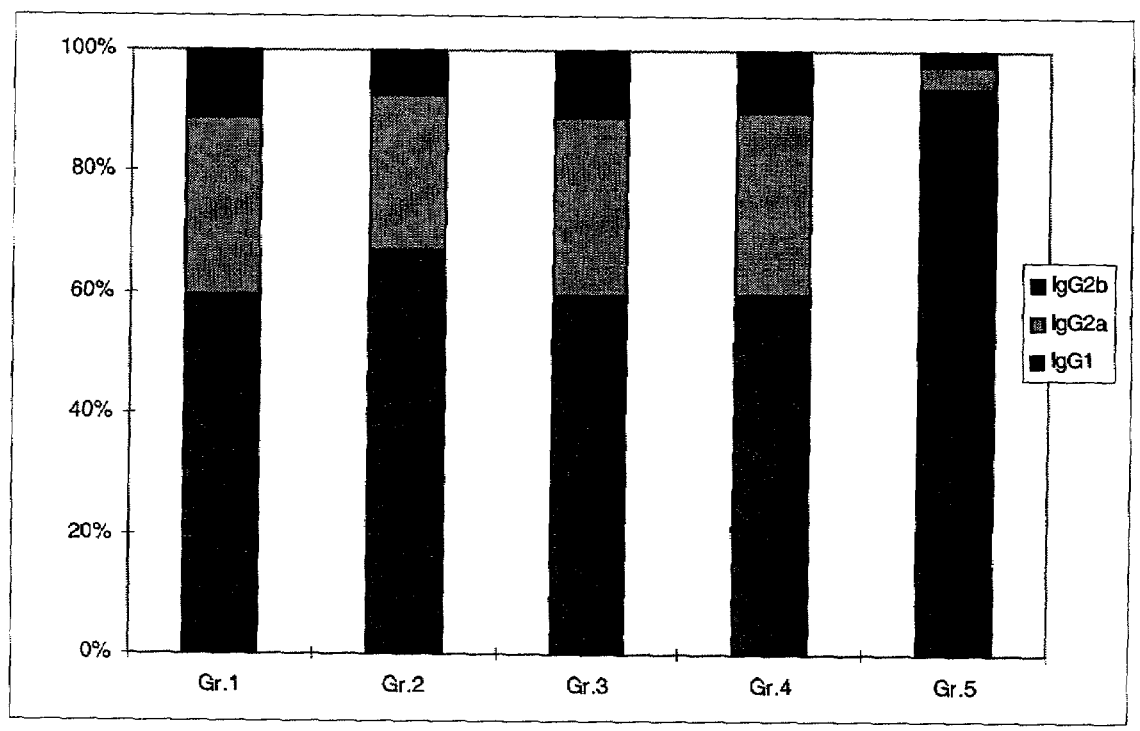
FIG. 2, Shows the sub-isotype distribution of Hbs specific IgG in the serum the vaccinated mice.

FIG. 2, Shows the sub-isotype distribution of Hbs specific IgG in the serum the vaccinated mice.

- As can be seen in FIG. 1, SB62 related formulations induce much higher antibody titers than the S,L* Alum formulation.
- Statistical analysis on individual sera (Anoval test Newman Keuls) show no significant difference in antibody titers induced by SB62c and SB62'c or equally between the antibody titers induced by SB62 and SB62'c. The resultant anti-S,L* antibody titres are, therefore, independent of the squalene:QS21 ratio.
- The sub-isotypic distribution profile (as shown in FIG. 2) is comparable for all SB62 related formulations (25-30% IgG2a) whereas Alum induce only 4% IgG2a.

Cell-Mediated Immune Responses

Cell-mediated immune responses (lymphoproliferation, IFNγ/IL5 production and CTL) were measured at 14 days post IV after in vitro restimulation of splenic and iliac lymph nodes cells with S,L* antigen.

Cytokine Production

Cytokine production (IFN-γ and IL-5) has been measured following 96 h of in vitro restimulation of splenic cells and iliac lymph node cells with S,L*. These results are depicted in FIGS. 3 to 6.

Figure 3:
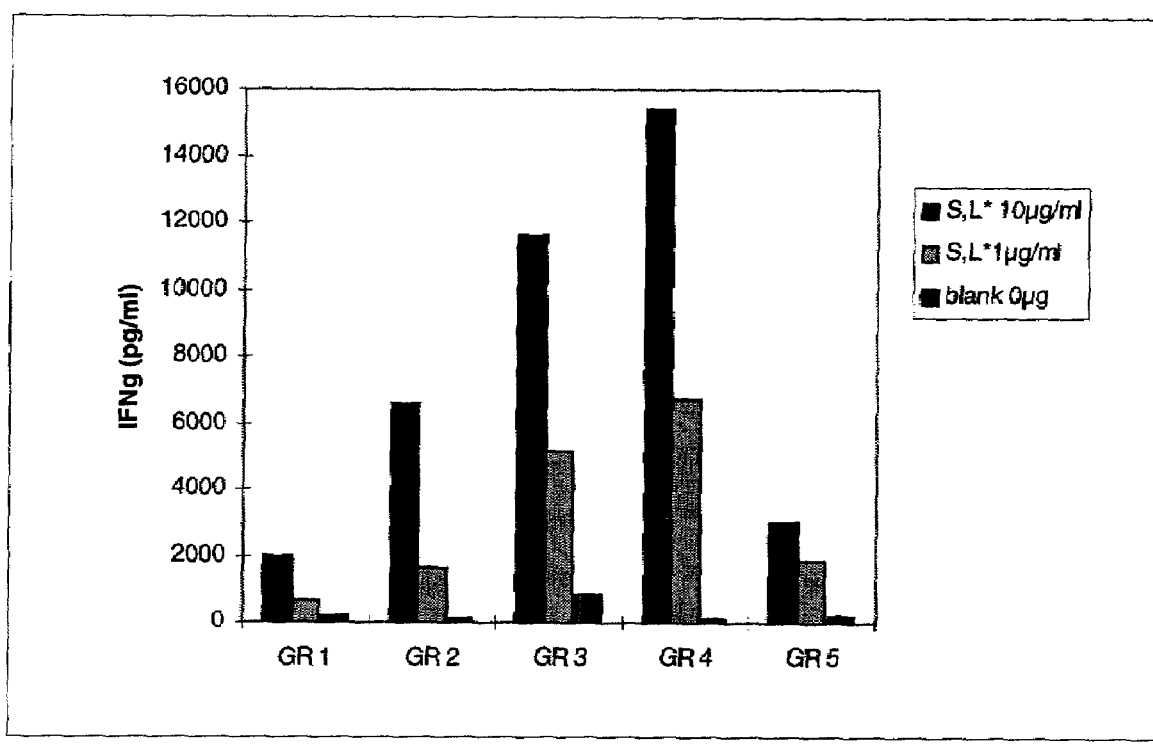
FIG. 3, Shows the results of IFN-y production by splenic cells (mean of data obtained with three pools/group).

FIG. 3, Shows the results of IFN-γ production by splenic cells (mean of data obtained with three pools/group).

Figure 4:
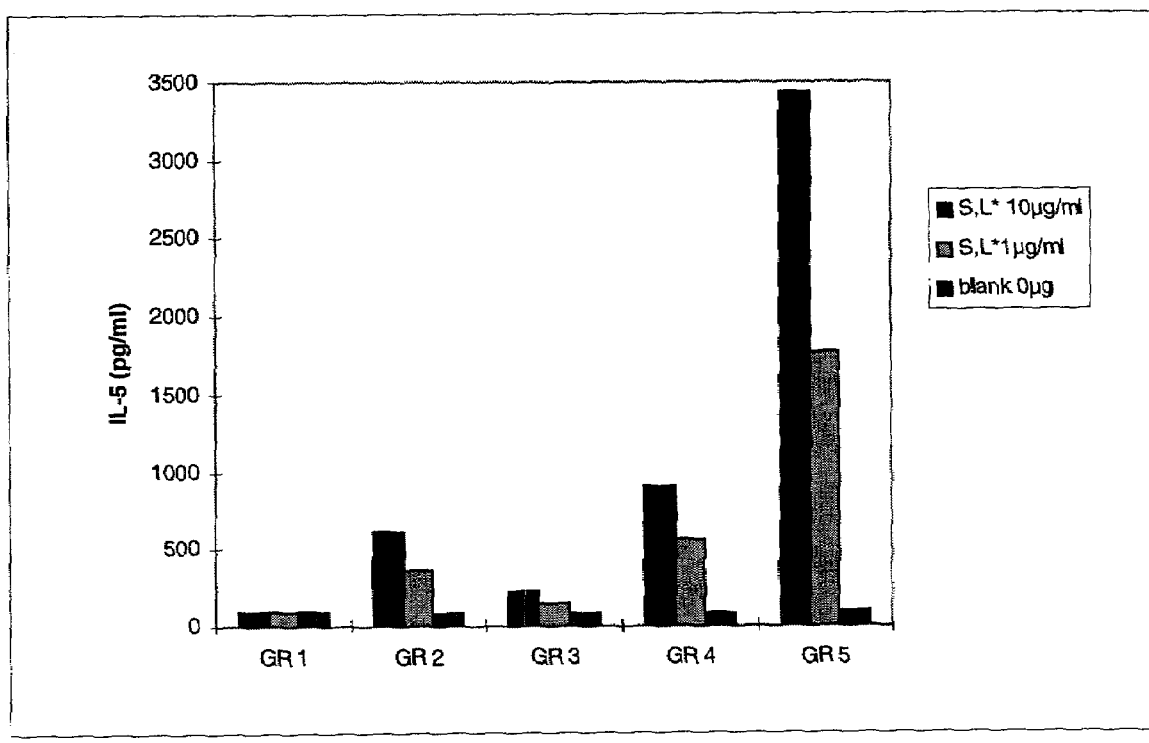
FIG. 4, Shows the results of IL-5 production by splenic cells (mean of data obtained with three pools/group).

FIG. 4, Shows the results of IL-5 production by splenic cells (mean of data obtained with three pools/group).

Figure 5:
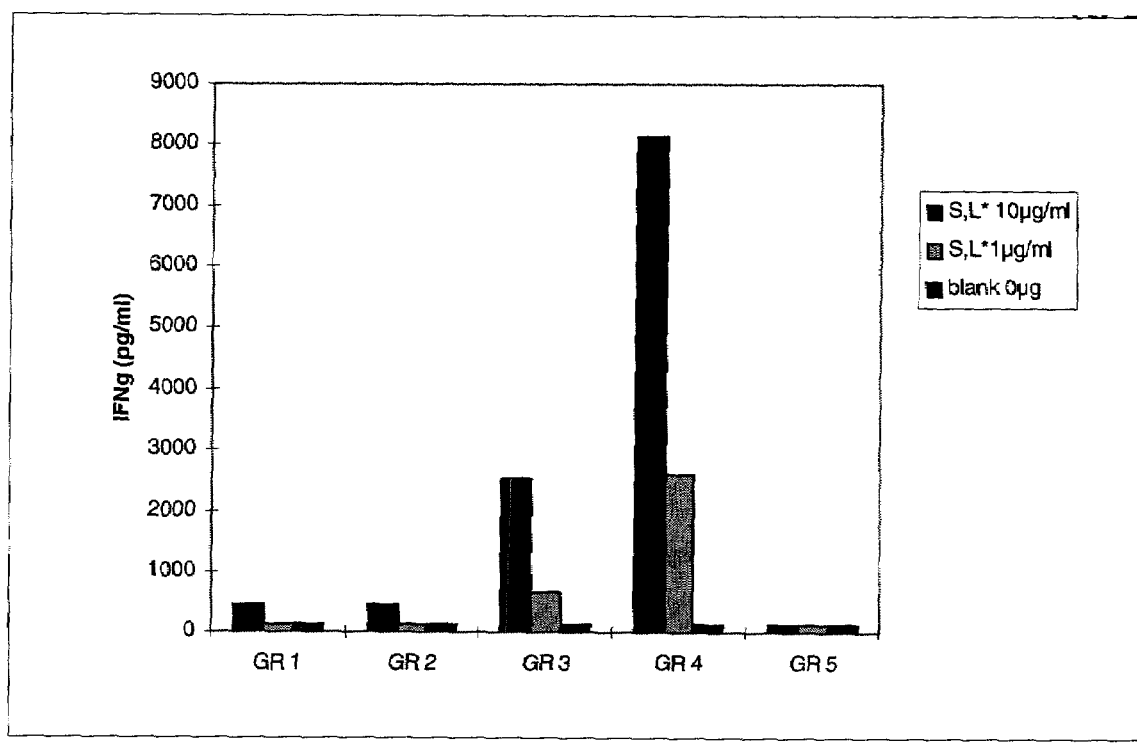
FIG. 5, Shows the results of IFN-y production by Iliac lymph node cells (mean of data obtained with three pools/group).

FIG. 5, Shows the results of IFN-γ production by Iliac lymph node cells (mean of data obtained with three pools/group).

Figure 6:
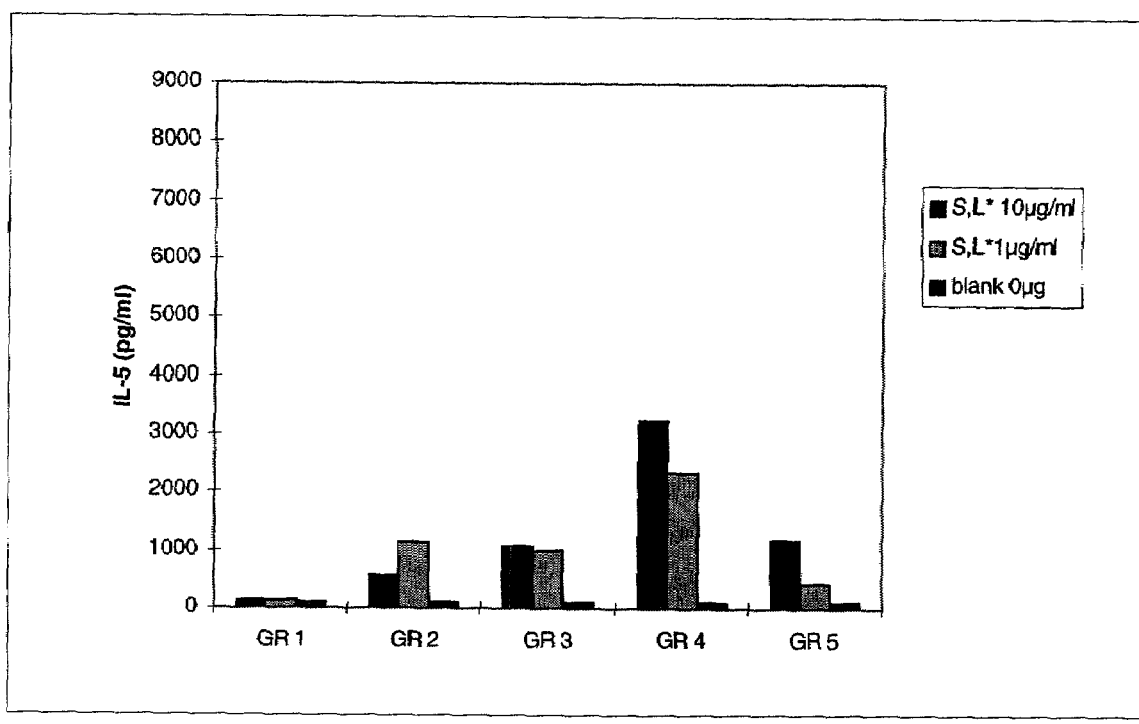
FIG. 6, Shows the results of IL-5 production by Iliac lymph node cells (mean of data obtained with three pools/group).

FIG. 6, Shows the results of IL-5 production by Iliac lymph node cells (mean of data obtained with three pools/group).

TABLE 2

Ratio of IFN-γ:IL-5 producing cells detected in splenic cells

| Restimulation | Groups | | | | |
| --- | --- | --- | --- | --- | --- |
|  | GR 1 | GR 2 | GR 3 | GR 4 | GR 5 |
| S,L* 10 µg/ml | 22.9 | 10.7 | 51.7 | 17.0 | 0.9 |

Discussion

Smaller amounts of emulsion are beneficial to IFN-γ production. Very high levels of INF-γ are produced after by restimulation of splenic cells from animals immunised with formulations containing the low ratio emulsion. These levels are significantly greater than those obtained after vaccination with corresponding formulations using a full dose emulsion. The strongest IFN-γ production is obtained after restimulation of splenic cells from animals immunised with S,L* SB62 and SB62'c.

The beneficial effect of the low ratio formulations (groups 3 and 4 on FIGS. 5 and 6) are much more marked when looking at cells derived from the draining lymph node (ileac lymph node) compared to those taken from the spleen.

An IFN-γ:IL-5 ratio >1 clearly suggests that a pro TH1 response is induced by all SB62 related formulations (see table 1).

Higher levels of IL-5 are produced by animals immunised with S,L* SB62c formulations than S,L* SB62 formulations not containing cholesterol. S,L* Alum immunised animals produce the highest levels of IL-5.

A stronger IFN-γ production is observed when the low ratio squalene:QS21 formulations (SB62' and SB62'c) are used.

Cytotoxic T Cell Response

Figure 7:
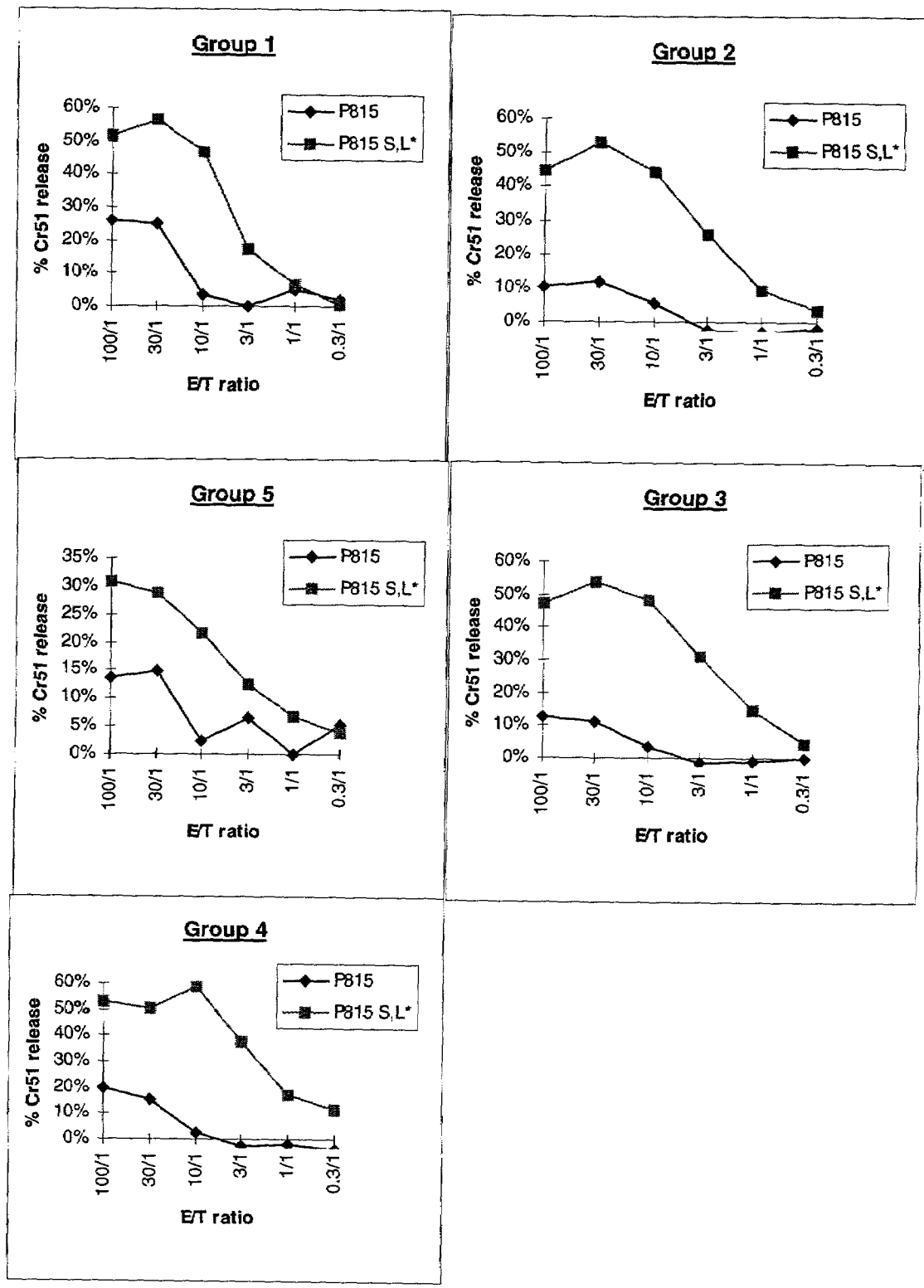
FIG. 7, Shows the CTL activity of splenic Tcells stimulated in vitro for 7 days with S,L* antigen (mean % specific lysis of three pools).

The anti-S,L* CTL responses are given in FIG. 7.

FIG. 7, Shows the CTL activity of splenic T-cells stimulated in vitro for 7 days with S,L* antigen (mean % specific lysis of three pools).

Discussion of CTL Results

Specific lysis is obtained with all oil in water emulsion formulations.

A stronger CTL response is observed with formulations containing SB62' emulsions when looking at limiting E/T ratio such as 3/1.

Conclusions

1. The strongest IFN-γ production is observed following immunisation with SB62' emulsions.
2. A slightly better CTL response is induced by formulations containing SB62' emulsions in comparison to the corresponding formulation using a full dose emulsion.
3. The TH1 type profile of the immune response induced by all SB62 related formulations is further confirmed by the IFN-γ/IL-5 ratio.
4. No significant difference is observed between antibody titers induced following immunisation with SB62c fill dose or SB62'c.
5. No significant difference is observed between antibody titers induced following immunisation with SB62c and SB62'.
6. A comparable isotypic profile (25-30% IgG2a) is obtained with all SB62 related formulations suggesting the induction of a TH1 type HBs specific immune response.

TABLE 3

Summary table showing the results from example 2.

| Immune parameter | Formulations containing S,L* | | | | |
|---|---|---|---|---|---|
| | SB62 | SB62c | SB62' | SB62'c | Alum |
| Ab titers | +++ | +++ | ++ | +++ | + |
| TH type | TH1 | TH1 | TH1 | TH1 | TH2 |
| (% IgG2a) | (29) | (26) | (29) | (30) | (4) |
| IFN-γ (SPC) | + | ++ | +++ | ++++ | + |
| IL-5 (SPC) | − | + | + | ++ | +++ |
| CTL | + | + | ++ | ++ | − |

EXAMPLE 3

Immunogenicity Studies with Malaria Antigens TRAP and RTS,S

Immunisation experiments using the *Plasmodium falciparum* Malaria antigens TRAP and RTS,S in combination with various adjuvants, each based on an oil in water emulsion system. RTS is a hybrid protein comprising substantially all the C-terminal portion of the circumsporozoite (CS) protein of *P. falciparum* linked via four amino acids of the preS$_2$ portion of Hepatitis B surface antigen to the surface (S) antigen of hepatitis B virus. If s full structure is disclosed in the International Patent Application No. PCT/EP92/0259 1, published under Number WO 93/10152 claiming priority from UK patent application No.9124390.7. When expressed in yeast RTS is produced as a lipoprotein particle, and when it is co-expressed with the S antigen from HBV it produces a mixed particle known as RTS,S.

TRAP antigens are described in the International Patent Application No. PCT/GB89/00895, published under WO 90/01496. TRAP antigens are polypeptides, so called Thrombospondin Related Anonymous Proteins, which share homology with various *P. falciparum* proteins.

Different adjuvant formulations, using the emulsion systems as described in example 1, with differing ratios of squalene:QS21, and optionally comprising cholesterol (QS21:cholesterol ratio w/w of 1:10), were combined with the malaria antigens and compared in their ability to induce humoral and cell mediated immune responses (T-cell proliferation and cytokine production). SB62 was formulated together with the antigen at a high (240:1, SB62) or low (48:1, SB62') ratio of squalene:QS21, optionally with the addition of cholesterol (c).

Groups of 5 mice (six week old female mice, strain C57/BL6×CBA/J [H-2k]) were immunised twice (in 2×50 μl volumes) in the hind foot-pad, 14 days apart, with either 10 μg RTS,S or 4 μg TRAP combined with various oil in water emulsion systems (SB62). 14 days following the second immunisation the production of cytokines (IL5 and IFN-γ) and T-cell proliferation was analysed after in vitro restimulation of spleen and lymph nodes cells with the malaria antigens. Antibody response to RTS,S and TRAP and the isotypic profile that was induced was investigated by ELISA.

TABLE 4

Groups of animals and vaccine formulations used in example 3.

| Group No. | Antigen | Adjuvant |
|---|---|---|
| 1 | RTS,S | SB62/QS21/3D-MPL |
| 2 | TRAP | SB62/QS21/3D-MPL |
| 3 | RTS,S/TRAP | SB62/QS21/3D-MPL |
| 4 | RTS,S | AlOH/QS21/3D-MPL |
| 5 | RTS,S/TRAP | AlOH/QS21/3D-MPL |
| 6 | RTS,S | SB62c/QS21/3D-MPL |
| 7 | RTS,S/TRAP | SB62c/QS21/3D-MPL |
| 8 | RTS,S | SB62'/QS21/3D-MPL |
| 9 | RTS,S/TRAP | SB62'/QS21/3D-MPL |
| 10 | — | SB62/QS21/3D-MPL |
| 11 | Vac. Vir. 3D7 | |

Footnotes:
SB62—oil in water emulsion full dose
SB62'—oil in water emulsion exemplified in the FIGS. as SB62 ⅕th dose
SB62c or SB62'c—oil in water emulsion (either dose) plus cholesterol in the oil phase.
Vac. Vir. 3D7 = a recombinant vaccinia virus construct expressing CS protein and administered at 10$^6$ PFU per mouse.

T-Cell Proliferation

Spleen or popliteal lymph node cells were aseptically removed and washed. 100 µl of cells in RPMI medium (1% heat-inactivated normal mouse serum, NMS) containing $2 \times 10^6$/ml of cells were cultured in round bottomed plates in the presence of RTS,S or TRAP antigens. Following stimulation for 96 hours with 0.1, 0.5, and 2.5 µg of antigen, or 48 hours with 2 µg/ml ConA, the cells were labelled with $^3$H-Thymidine (1 µCi/well) for 16 hours before harvesting and counting in a β-counter.

RPMI Medium:

RPMI 1640 without L-glutamine (Life technologies No.31870025), 2 mM L-glutamine (Life technologies No.25030024), 50 µM 2-Mercaptoethanol (Life technologies No.11360039), 1 mM Sodium Pyruvate (Life technologies No.11360039), 1×MEM non essential amino acids (10×stock, Life technologies No.11140035), 100 IU/ml penicillin—100 µg/ml streptomycin (Life technologies No.15140114).

Cytokine Detection

Spleen or popliteal lymph node cells were aseptically removed and washed. 1000 µl of cells in RPMI medium (5% heat-inactivated fetal calf serum, FCS) containing $5 \times 10^6$/ml of cells were cultured in 24 well flat bottomed plates in the presence of RTS,S or TRAP antigens. The plates were then incubated (37° C., 5% $CO_2$) for a number of hours with 0.5, and 2.5 µg of antigen, or 4 µg/ml final of ConA.

The length of time that the cells were incubated depended on the particular cytokine to be detected, IL-2 was stimulated for 72 hours, IL-5 was 72 or 96 hours, and IFN-γ was 96 hours. Each cytokine was detected using commercially available ELISA kits (IL-2 and IFN-γ, Duoset Genzyme No.80-3573-00 and 80-3931-00 respectively; IL-5 was detected using the Pharmingen kit).

Serology

Antibodies directed against TRAP were analysed using a sandwich ELISA. A sheep anti-TRAP antiserum was coated onto ELISA plates which was used to capture TRAP antigen added at 0.5 µg/ml. Titrations of pooled serum from the experimental groups were added and incubated. Finally, biotinylated anti-mouse isotype-specific antibodies followed by streptavidin-peroxidase, were used to detect bound TRAP-specific antibodies.

Anti HBV humoral responses were analysed by a direct ELISA, HBsAg was coated onto the ELISA plate at 1 µg/ml. Pooled serum from the different experimental groups were titrated and bound antibodies were detected as described above.

Results

Proliferation of Lymphoid Cells in Response to Antigen

The proliferative responses in response to antigen can be seen in FIGS. 8 to 11. All vaccine preparations stimulated cells in the local popliteal lymph node which were capable of proliferating in vitro in response to antigen, the magnitude of which was independent of the addition of cholesterol.

All vaccine preparations were capable of stimulating splenic cells which proliferated in vitro in response to antigen. When considering the stimulation indices, the preparations which elicited the highest responses in the spleen were the ones having the low ratio squalene:QS21 (48:1 or ⅕ th dose SB62).

Figure 8:
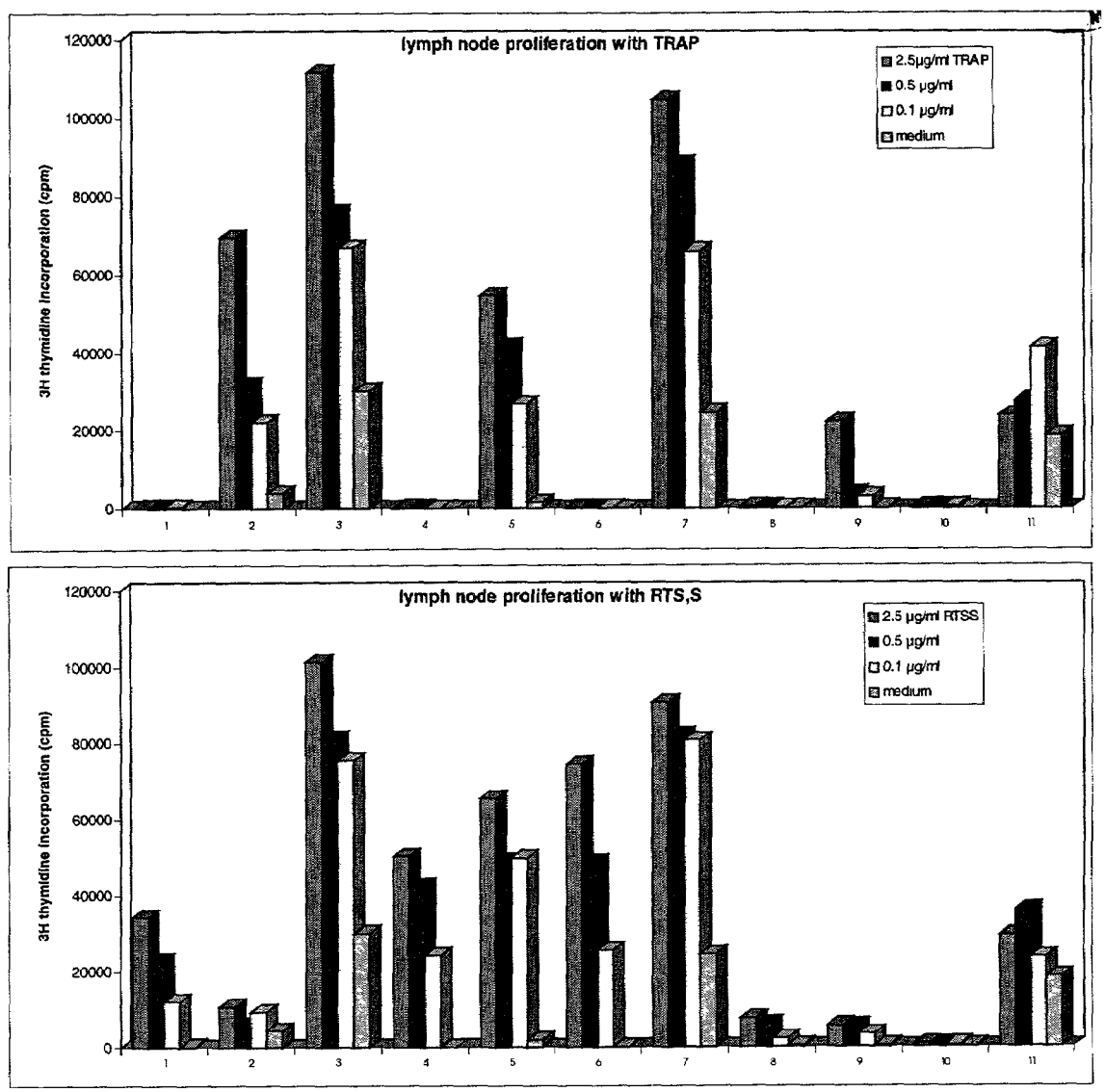
FIG. 8, Shows the proliferative responses of popliteal lymph node cells (in raw counts per minute (CPM) form) derived from the experimental groups after stimulation with TRAP and RTS,S antigens.

FIG. 8, Shows the proliferative responses of popliteal lymph node cells (in raw counts per minute (CPM) form) derived from the experimental groups after stimulation with TRAP and RTS,S antigens.

Figure 9:
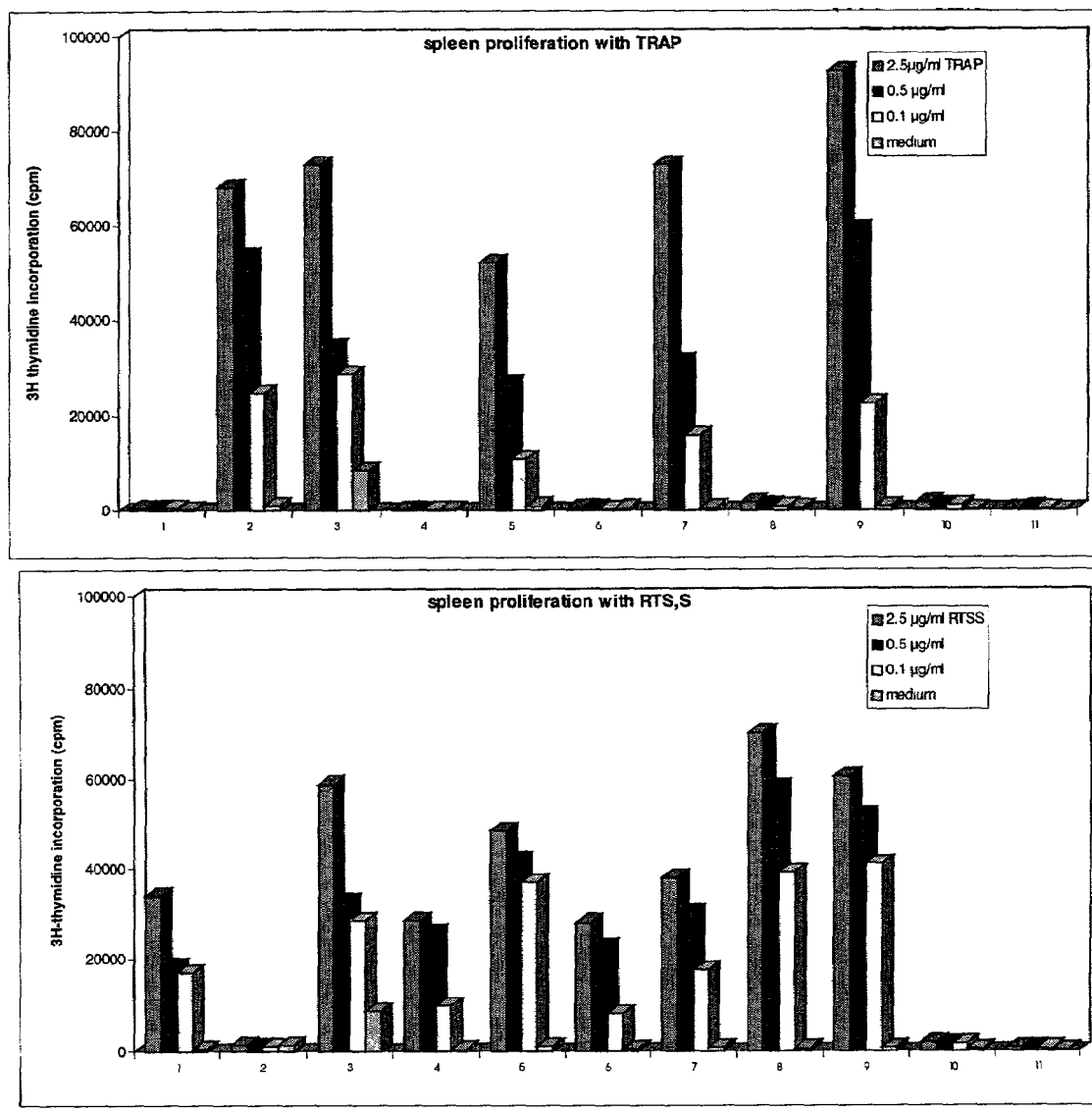
FIG. 9, Shows the proliferative responses of splenic cells (in raw counts per minute (CPM) form) derived from the experimental groups after stimulation with TRAP and RTS,S antigens.

FIG. 9, Shows the proliferative responses of splenic cells (in raw counts per minute (CPM) form) derived from the experimental groups after stimulation with TRAP and RTS,S antigens.

Figure 10:
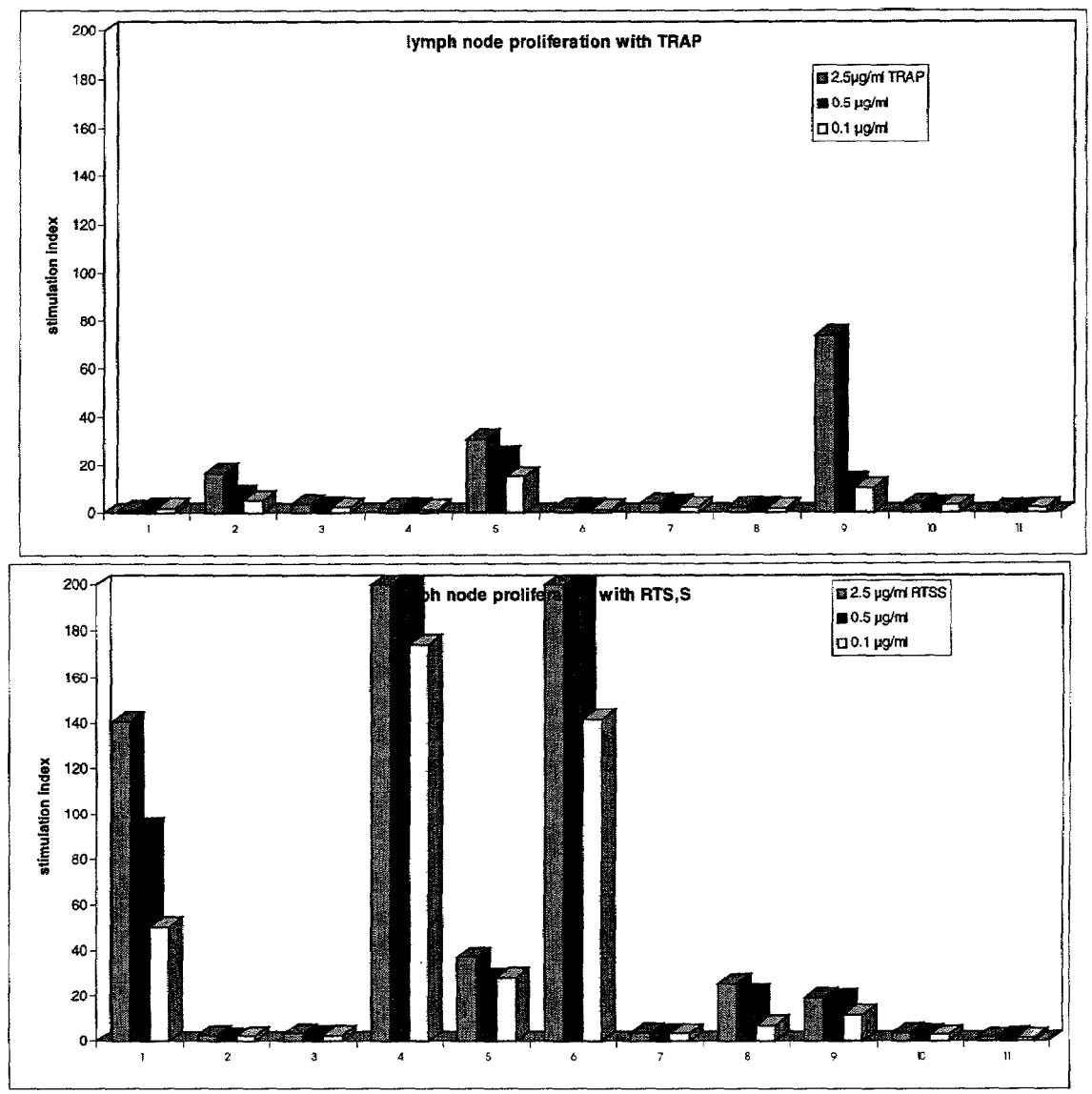
FIG. 10, showing the proliferative responses of popliteal lymph node cells (Stimulation index) derived from the experimental groups after stimulation with TRAP and RTS,S antigens.

FIG. 10, showing the proliferative responses of popliteal lymph node cells (Stimulation index) derived from the experimental groups after stimulation with TRAP and RTS,S antigens.

Figure 11:
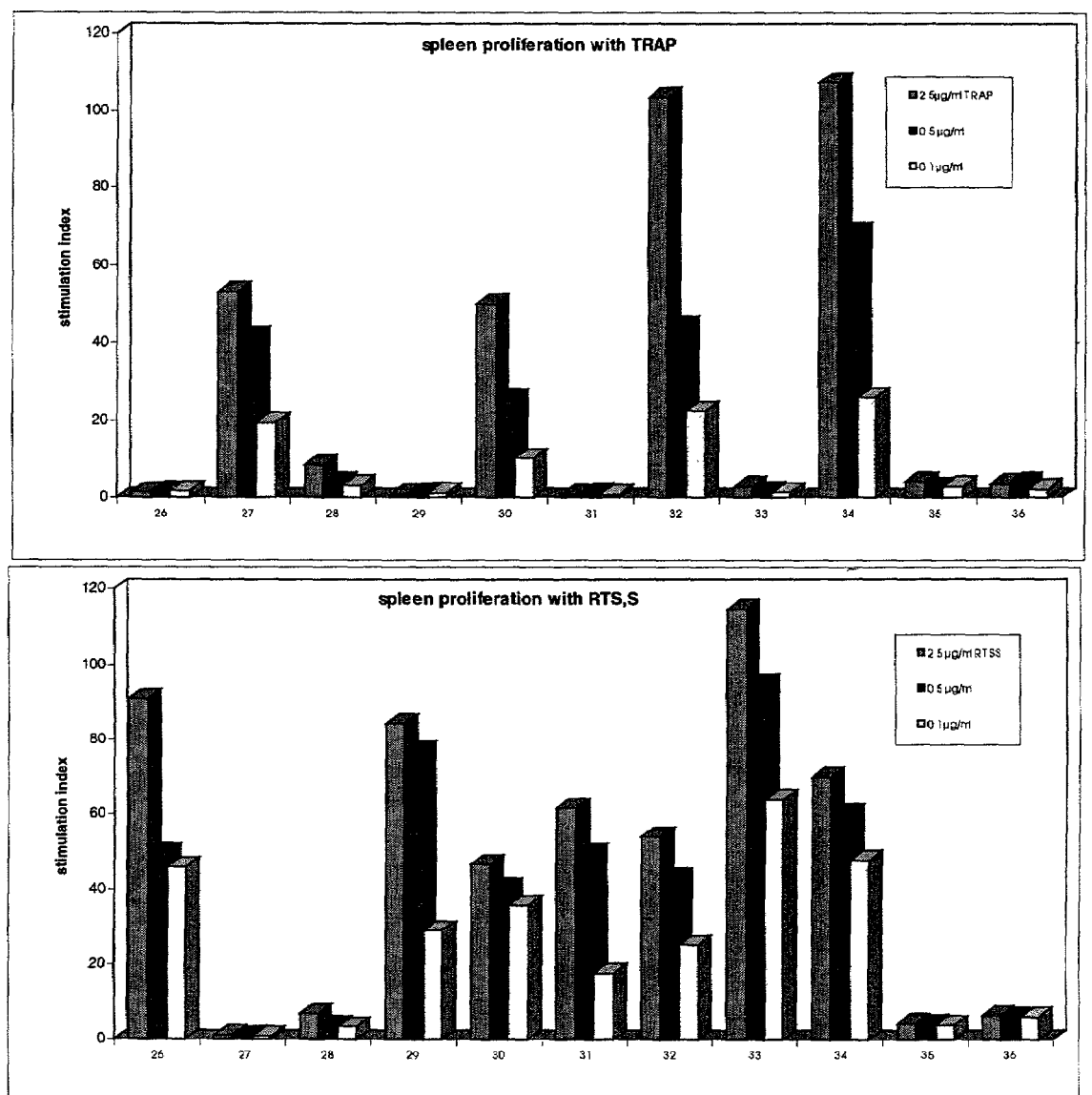
FIG. 11, Shows the proliferative responses of splenic cells (Stimulation index) derived from the experimental groups after stimulation with TRAP and RTS,S antigens.

FIG. 11, Shows the proliferative responses of splenic cells (Stimulation index) derived from the experimental groups after stimulation with TRAP and RTS,S antigens.

Discussion of Proliferation Results

FIGS. 1 and 2, clearly show that all of the vaccine formulations stimulate lymphoid cells which are capable of proliferating in vitro in the presence of antigen in a dose dependent manner. The raw cpm data suggests that the inclusion of cholesterol in the adjuvant formulations has no effect on the magnitude of the proliferative responses (for example a comparison between groups 1 and 6, termed RTS,S/MPL/QS21/SB62 and RTS,S/MPL/QS21/SB62c respectively).

Examination of the cpm together with the stimulation index results (obtained by dividing the raw cpm for antigen specific proliferation by that derived from non-antigen specific proliferation (medium alone)) shows that the vaccine formulation which generates the highest proliferative responses depends on the origin of the lymphocyte measured. The adjuvant formulations containing the low ratio of squalene:QS21 (48:1) generate the highest proliferative responses in the spleen.

In Vitro Cytokine Production Upon Stimulation with Antigen

Cytokine production, measured in vitro in response to antigen, can be both a quantitative and qualitative measure of the induction of immune responses in vivo. In general high levels of IFN-γ and IL-2 are taken to be a measure of Th1-type immune responses and IL-5 is considered to be a Th2-type cytokine. The following figures (FIGS. 12 to 14) demonstrate the use of SB62', containing a reduced ratio of squalene:QS21 (termed SB62 ⅕th dose), had a marked effect in enhancing the production of IFN-γ (FIG. 6).

Further, there is evidence that the addition of cholesterol has no qualitative or quantitative effects on the cytokine profile produced in vitro in response to antigen. This effect may have significant consequences in the induction of Th1-type immune responses and also immunotherapeutics.

Figure 12:
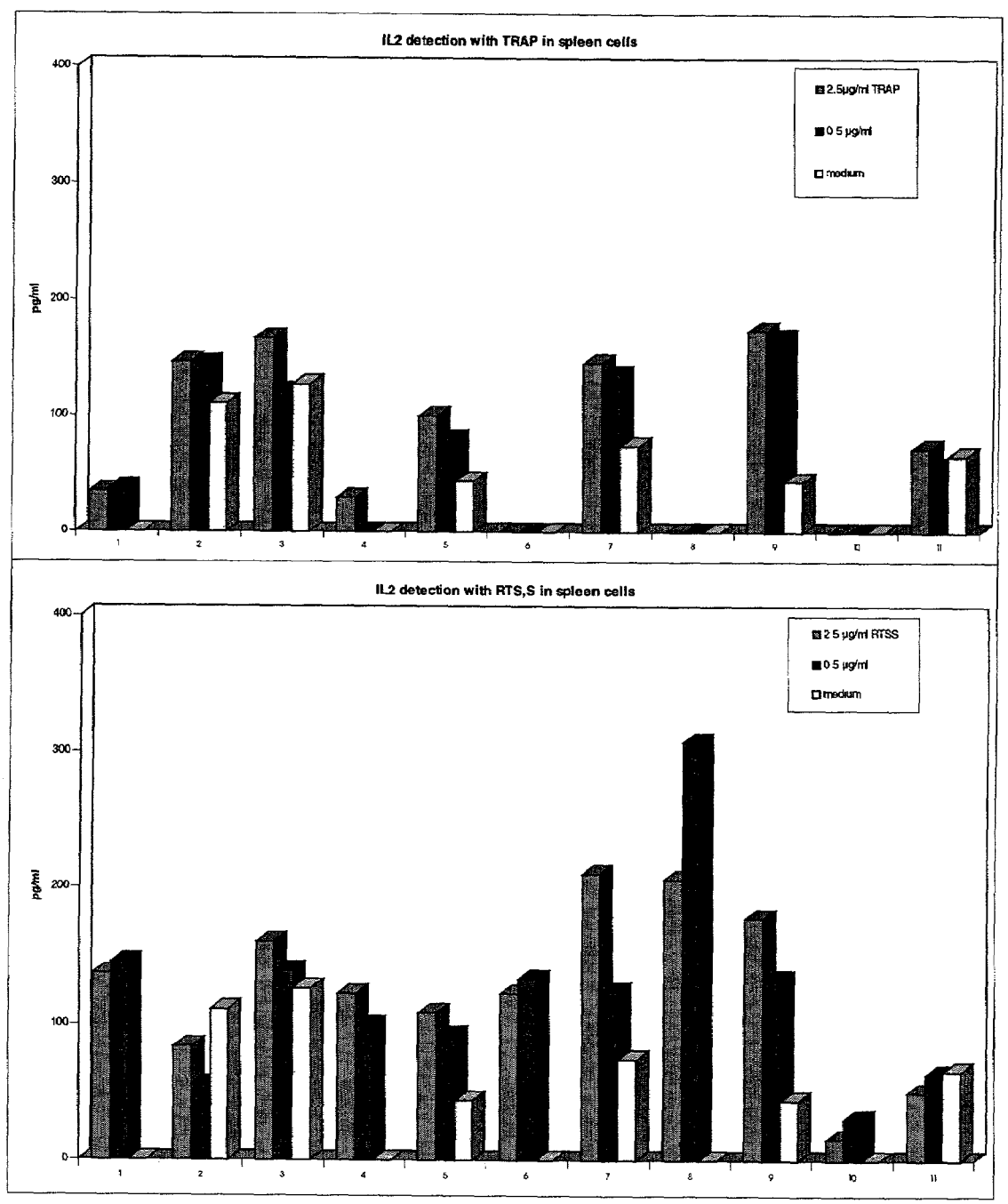
FIG. 12, Shows the IL-2 production of spleen cells after stimulation with TRAP or RTS,S antigen 14 days after VII.

FIG. 12, shows the IL-2 production of spleen cells after stimulation with TRAP or RTS,S antigen 14 days after VII.

Figure 13:
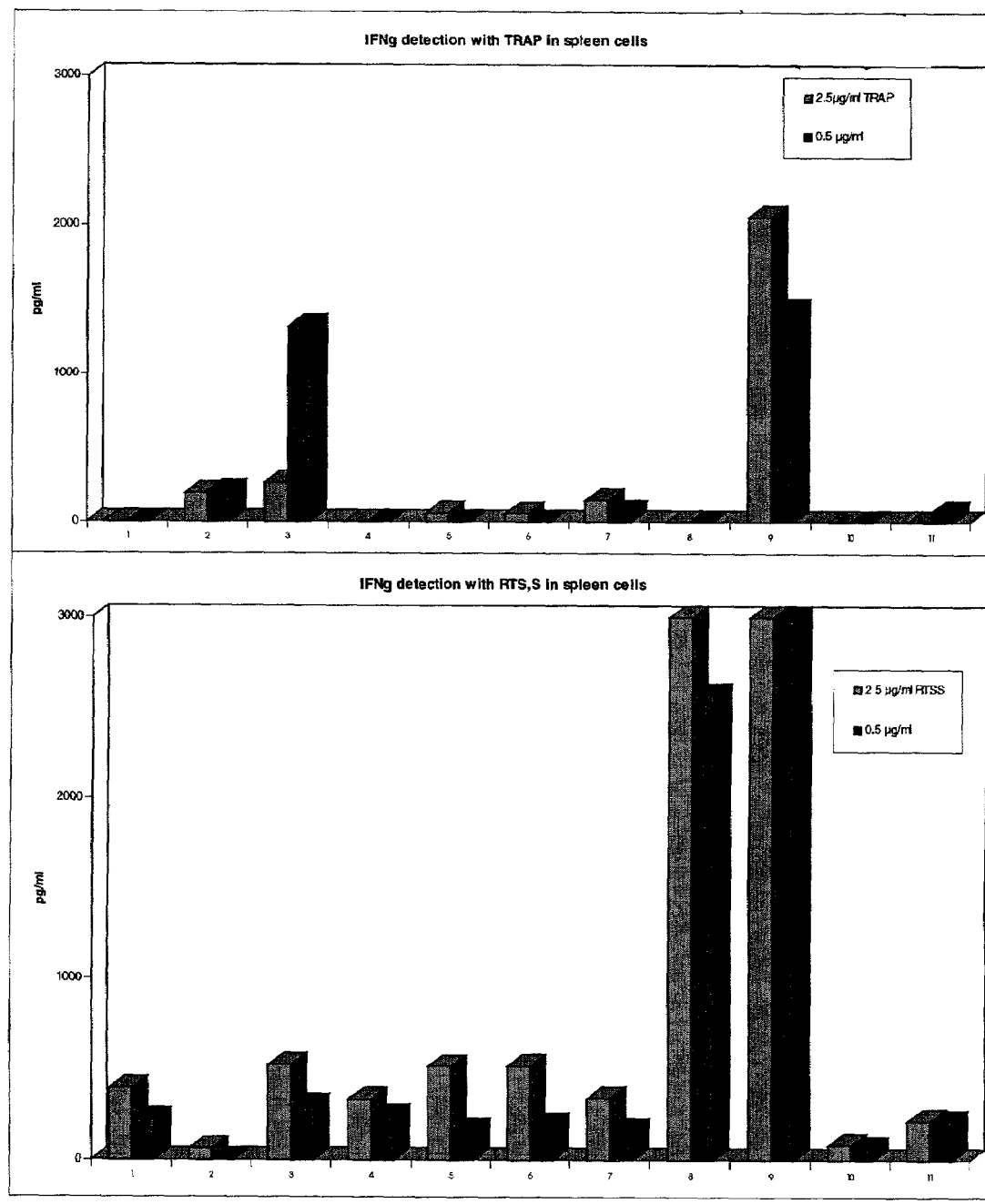
FIG. 13, Shows the IFN-y production by spleen cells after stimulation with TRAP or RTS,S antigen 14 days after VII.

FIG. 13, shows the IFN-γ production by spleen cells after stimulation with TRAP or RTS,S antigen 14 days after VII.

Figure 14:
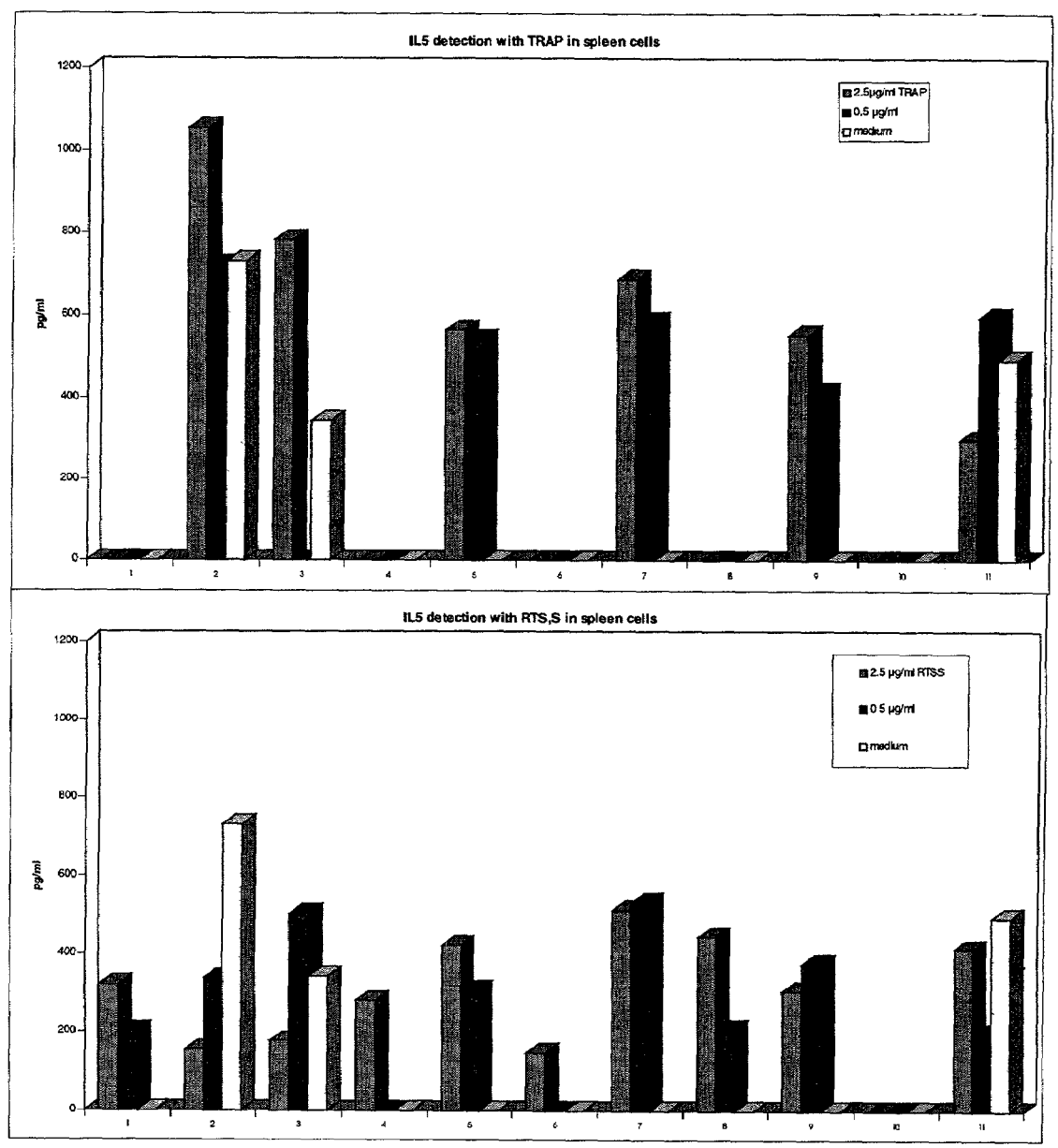
FIG. 14, Shows the IL-5 production by spleen cells after stimulation with TRAP or RTS,S antigen 14 days after VII.

FIG. 14, shows the IL-5 production by spleen cells after stimulation with TRAP or RTS,S antigen 14 days after VII.

Serology

Another measure of immunity that can correlate to a Th1-type, or alternatively a Th2-type, immune response is the IgG sub-isotype which is elicited. A preferential stimulation of the IgG1 sub-isotype is generally taken to be a measure of the induction of a Th2-type immune response, and conversely IgG2a and IgG2b is taken to be a measure of a Th1 type immune response.

ELISA studies were performed on pooled mouse serum and the mid-point titres for both the HBsAg and TRAP specific antibodies were ascertained. From these figues, the ratio of the antigen specific IgG1 and IgG2a mid-point titres was calculated and taken to be a measure of the Th1/Th2 balance of the humoral immune response (the results are shown in table 4).

TABLE 4

The ratio of IgG1:IgG2a, representing the Th1/Th2 balance. A ratio <1 represents a Th1-type immune response, a ratio of >1 indicating a Th2-type response.

Ratio of mid-point titres IgG1:IgG2a

| Group | HBsAg | TRAP |
|---|---|---|
| 1 | 0.44 | |
| 2 | | 0.36 |
| 3 | 1.46 | 1.68 |
| 4 | 0.37 | |
| 5 | 0.39 | 11.83 |
| 6 | 0.28 | |
| 7 | 0.2 | 7.21 |
| 8 | 0.66 | |
| 9 | 0.3 | 0.77 |

Discussion of Serological Results

Pools of mouse serum were analysed from each group and were found to have successfully stimulated HBsAg and TRAP specific antibodies. In general, antibody mid-point titres against HBsAg were higher than those found against TRAP. The isotype distribution differed between the two antigens. RTS,S in all formulations elicited a clear Th1 pattern, as indicated by an IgG1:IgG2a ratio below 1.

In contrast, TRAP-specific antibodies exhibited a Th2-type isotype pattern. The only exceptions to this observation were groups 2, who received TRAP alone, and group 9, who received TRAP/RTS,S in a SB62' formulation (containing a low ratio of squalene:QS21, termed SB62 ⅕th dose). The use of SB62' may, therefore, be useful in the design of Th1-inducing vaccines with antigens which are known to preferentially induce Th2-type immune responses.

EXAMPLE 4

Immunological Studies Using a Murine Tumour Regression Model

This experiment investigated the potential use of oil in water emulsion adjuvants for the therapeutic treatment of Human Papilloma virus (HPV) expressing tumors. Tumor cells (TC1), known to express the E7 protein of HPV 16, were innoculated into C57BL/66-8 weeks old mice. These tumor cells if left untreated grew into tumors of measurable size. The potential of E7 comprising vaccines, based on oil in water emulsion adjuvants, to prevent the establishment of these tumors was investigated. The therapeutic potential of various oil in water emulsions (for details see example 1) SB62 full-dose, SB62 ⅕, SB62c full-dose, and SB62c ⅕ in combination with ProtD⅓ E7 HPV16 recombinant antigen, was evaluated in the TC1-E7 tumor model. Further, the contribution of vaccination schedules were compared.

Briefly, groups of 8-10 C57BL/6 mice were challenged with 5×10⁵ TC1 tumour cells (in the flank). The groups of mice were then immunized intra-footpad with 5 μg ProtD⅓ E7 combined with various formulations, 7 and 14 days after a subcutaneous tumor challenge.

Other vaccination shemes were compared: 2 vaccinations with 5 μg ProtD/3 E7 in SB62 (days 14 and 21 after the tumor challenge); and 4 vaccinations with 5 μg ProtD⅓ E7 in SB62 (7, 14, 21, 28 days after tumor challenge).

Antibody responses to E7 were monitored by ELISA at time points, 2 and 4 weeks post second vacination. Lympho-proliferative response was analyzed by in vitro restimulation of spleen and lymph nodes cells for 72 hrs with the protein E7 (10, 1, 0.1 μg/ml) 2 and 4 weeks post second vaccination. CTL responses were measured after in vitro re-stimulation of spleen cells with irradiated tumor cells (TC1) or an E7-derived peptide. The Chromium release assay was performed on TC1 cells, on a syngeneic tumor cell line:EL4 pulsed or not with an E7-derived peptide or infected either with a E7 recombinant vaccinia virus or with the wild type vaccinia virus.

TABLE 5

Groups of mice

| Group | Vaccination schedule (days after challenge) | Antigen (HPV 16) | Exipient |
|---|---|---|---|
| a | 7, 14 | — | PBS |
| b | 7, 14 | ProtD1/3 E7 | PBS |
| c | 7, 14 | ProtD1/3 E7 | DQ |
| d | 7, 14 | — | DQ |
| e | 7, 14 | ProtD1/3 E7 | SB62 |
| f | 7, 14 | — | SB62 |
| g | 7, 14 | ProtD1/3 E7 | SB62' |
| h | 7, 14 | — | SB62' |
| i | 7, 14 | ProtD1/3 E7 | SB62c |
| j | 7, 14 | — | SB62c |
| k | 7, 14 | ProtD1/3 E7 | SB62'c |
| l | 7, 14 | — | SB62'c |
| m | 7, 14, 21, 28 | ProtD1/3 E7 | SB62 |
| n | 14, 21 | ProtD1/3 E7 | SB62 |

Therapeutic Experiments:Protocol
  5×10⁵ TC1-E7 expressing tumor cells were injected subcutaneously (200 μl) in the flank of C57BL/6 immunocompetent mice.
  Vaccinations were performed at either 7, 14, 21, or 28 days after the tumor challenge, with 5 μg ProtD ⅓ E7 HPV16 injected intra-footpad (100 μl:50 μl footpad). Each vaccine was formulated in the presence of different adjuvants: SB62, SB62c, SB62' or SB62'c.
  2 and 4 weeks after the second immunization, mice were killed and spleens or popliteal lymph nodes were taken and assayed in lymphoproliferation or CTL assays.

Comparative Liposome-Based Formulations (DO)

ProtD⅓-E7 antigen (5 μg) was incubated 30 min with MPL (5 μg) before buffer addition as a mix of 10 fold concentrated PBS pH 7.4 and H₂O. After 30 min, QS21 (5 μg) was added to the formulation mixed with liposomes in a weight ratio QS21/Cholesterol of 1:5 (referred to as DQ). 50 μg/ml of thiomersal were added to the formulation as preservative 30 min after addition of the QS21. All incubations were carried out at room temperature with agitation.

Cell Lines

TC1 (obtained from the John Hopkin's University), or EL4 cells were grown in RPMI 1640 (Bio Whittaker) containig 10% FCS and additives: 2 mM L-Glutamine, 1% antibiotics (10000 U/ml penicilin, 10000 μg/ml streptomycin) 1% non essential amino acid 100×, 1% sodium pyruvate (Gibco), 510e-5 M 2-mercaptoethanol. Before injection into the flank of the mice, the TC1 cells were trypsynized and washed in serum free medium.

Tumor Growth

Individual tumor growth was followed over time. The 2 main diameters (A, B) were measured using calipers twice a week, A×B represents the "tumor surface" and is expressed as the average of the 5 values in each group.

In Vitro Lymphoproliferation

Lymphoproliferation was performed on individual spleens and on lymph node pools. The cell suspension were incubated with Tris-buffered ammonium chloride for 4 min at 4° C. in order to lyse the red blood cells. $2 \times 10^5$ spleen cells or popliteal lymph node cells were plated in triplicate, in 96 well microplate, in RPMI medium containing 1% normal mouse serum. After 72 hrs incubation with different amounts of E7 (10-1-0.1 µg/ml), 100 µl of culture supernatant were removed and replaced by fresh medium containing 1 µCi $^3$H-thymidine. After pulsing for 16 hrs, the cells were harvested onto filter plates. Incorporated radioactivity was counted in a β counter. Results are expressed in counts per minute (CPM, mean of triplicate wells) or as stimulation indexes (mean CPM in cultures with antigen . mean CPM in cultures without antigen).

CTL Assay $2 \times 10^6$ spleen cells were co-cultured with $2 \times 10^6$ irradiated (18000 rads) TC1 cells for 7 days. Target cells were either $Cr^{51}$ (DuPont NEN 37MBq/ml) loaded (1 hr at 37° C.) TC1 cells or EL4 cells (syngeneic tumor cells) infected with an E7 recombinant vaccinia virus (received from T. C. Wu from the John Hopkins University). The results derived from these cells were compared to those from EL4 targets which had been infected with the wild type vaccinia virus (Vaccinia infection is performed at a MOI of 10 in a small volume of serum free medium, for 1H, at 37° C. in a $CO_2$ incubator. Fresh medium was added and cells were incubated overnight before use). 10 µg/ml of E7-derived peptide (49-57) (QCB) was used to pulse EL4 cells for 1 hr at 37° C. during the $Cr^{51}$ loading of the cells. 2000 target cells were added to each well of 96 well plate (V botttom nunc 2-45128) with 100/1 being the highest Effector/target ratio. Controls for spontaneous or maximal $Cr^{51}$ release were performed in sextuplet and were targets in medium or in triton 1.5%. All plates were gently centrifuged and incubated for 4 hrs at 37 in 7% CO2. 50 µl of the supernatant was deposed on 96w Lumaplate (Packard) let dry O/N and counted in a Top Count counter. Data is expressed as percent specific lysis which is calculated from the c.p.m. by the formula (experimental release–spontaneous release)÷. (maximal release–spontaneous release)×100.

Serology

Quantitation of anti E7 antibody was performed by Elisa using E7 as coating antigen. Antigen and antibody solutions were used at 50 µl per well. Antigen was diluted at a final concentration of 3 µg/ml in carbonate buffer ph9.5 and was adsorbed overnight at 4° C. to the wells of 96 wells microtiter plates (Maxisorb Immuno-plate, Nunc, Denmark). The plates were then incubated for 1 hr at 37° C. with PBS containing 1% bovine serum albumin and 0.1% Tween 20 (saturation buffer). Two-fold dilutions of sera (starting at 1/100 dilution) in the saturation buffer were added to the E7-coated plates and incubated for 1 hr 30 min at 37° C. The plates were washed 3 times with PBS 0.1% Tween 20 and biotin-conjugated anti-mouse IgG1, IgG2a or IgG2b or IgGtot (Amersham, UK) diluted 1/5000 in saturation buffer was added to each well and incubated for 1 hr 30 min at 37° C. After a washing step, streptavidin-biotinylated peroxydase complex (Amersham, UK) diluted 1/5000 in saturation buffer was added for an additional 30 min at 37° C. Plates were washed as above and incubated for 10 min with TMB(tetra-methyl-benzidine) The reaction was stopped with $H_2SO_4$ 4N and read at 450 nm. Midpoint dilution were calculated by SoftmaxPro (using a four parameters equation).

Immunohistochemistry

Tumours were excised and fixed in acetone and paraformaldehyde prior to sectioning. The 5 µm thick cryostat secetions were then investigated and stained for CD4, CD8, and CD3 expressing T-cells infiltration. Prior to the addition of the staining monoclonal antibodies, the sections were washed and saturated with 0.5% bovine serum albumin (BSA), 5% normal rabbit serum (NRS) in PBS. After this step the rat anti-CD3, CD4, and CD8 monoclonal antibodies were added and incubated overnight at 4C. The sections were then washed and the binding of the rat monoclonal antibodies was revealed with biotinylated rabbit anti-rat Ig. After incubation for 30 mins, at room temperature (RT), streptavidin-Horse radish peroxidase was added and incubated for another 30 mins at RT. The binding of the streptavidin-Horse radish peroxidase was revealed with DAB for 10 minutes at RT. The sections were then counterstained with Hematoxylin, and dehydrated with ethanol, isopropanol, and finally xylol.

Results

Figure 15:
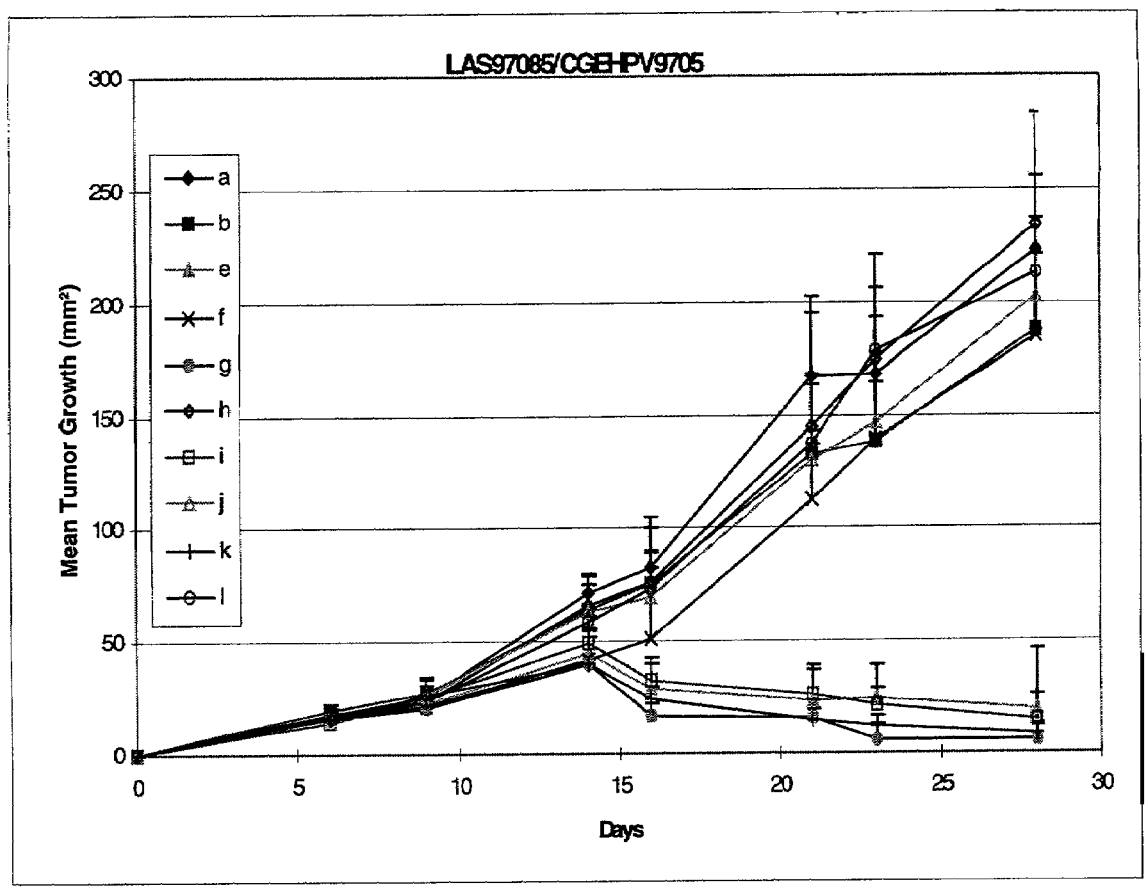
FIG. 15, Shows mean tumor growth after challenge and vaccination on days 7 and 14 with various ProtDI/3 E7 containing formulations.

Tumor growth (for a representation of the mean tumor growth/group see FIG. 15)

FIG. 15, Shows mean tumour growth after challenge and vaccination on days 7 and 14 with various ProtD⅓ E7 containing formulations.

Figure 16:
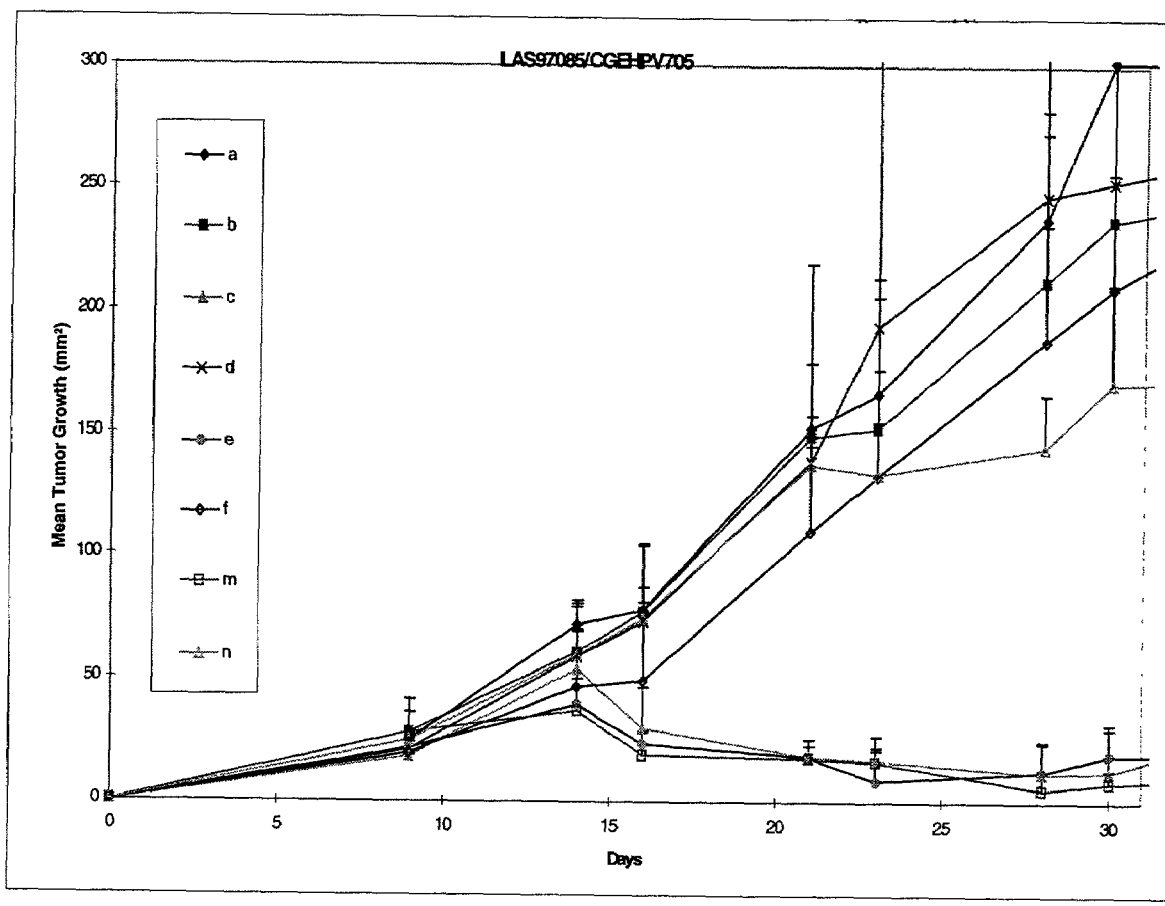
FIG. 16, Shows the mean tumor growth observed over a period of 4 weeks for the groups receiving the antigen in DQ and SB62 formulations, also represented are the results comparing the different vaccination schedules.

FIG. 16, Shows the mean tumor growth observed over a period of 4 weeks for the groups receiving the antigen in DQ and SB62 formulations, also represented are the results comparing the different vaccination schedules. These vaccines were administered on days 7 and 14; or days 14 and 21; or days 7, 14, 21, and 28.

FIG. 16, Comparison with comparative formulations and other vaccination schedules.

Discussion of the Tumour Regression Studies with the ProtD⅓ E7 antigen.

Vaccination with either ProtD⅓ E7 or adjuvant alone has no effect on the growth of the TC1-E7 expressing tumour.

The analysis of individual tumor growth showed complete tumour rejection in several groups:

| Group | Percentage tumour rejection |
|---|---|
| c | 40% |
| e | 40% |
| g | 60% |
| j | 20% |
| l | 10% |

The best formulation to induce tumor rejection were formulated with the low dose SB62' oil in water emulsion.

A better therapeutic effect was observed after 4 vaccinations than seen after 2. Analysis of individual tumor growth showed that 60% of the animals completely rejected their tumor after 4 vaccinations with a SB62 based formulation whilst only 40% of mice having received 2 vaccinations showed complete regression.

If the first vaccination was delayed until day 14 following the tumor challenge, no complete rejection could be observed. However, the tumor growth seemed to be abrogated.

Figure 17:
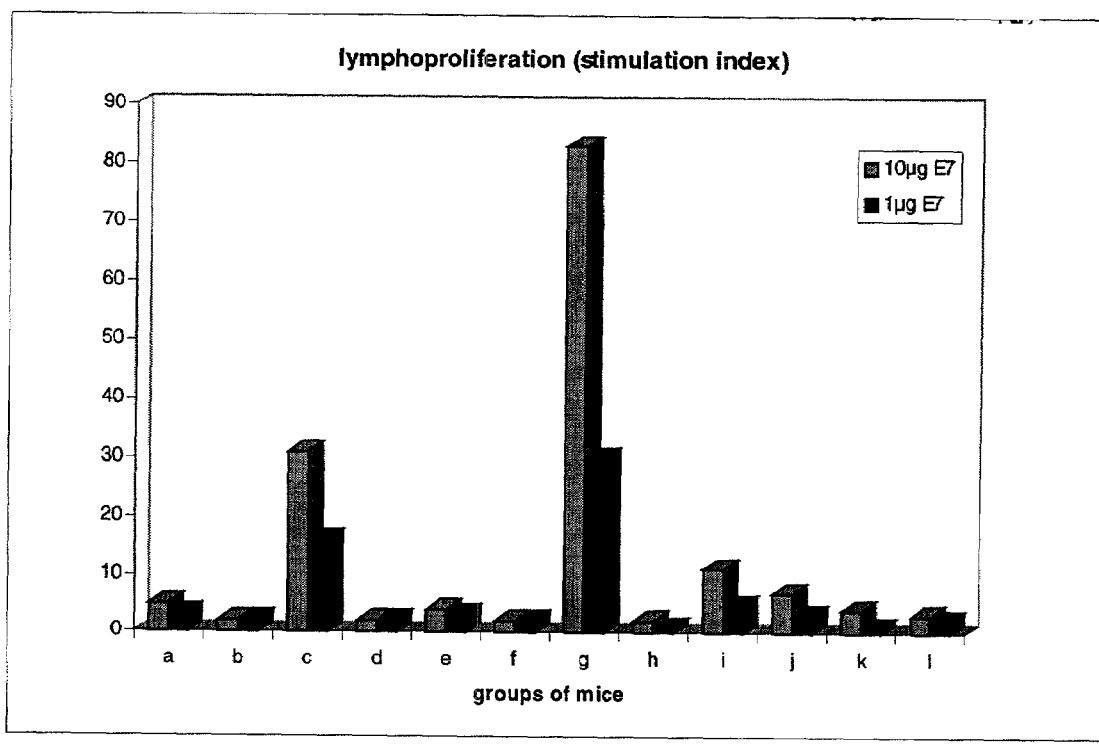
FIG. 17, Lymphoproliferation observed in spleen cells, 2 weeks after the second vaccination.
Figure 18:
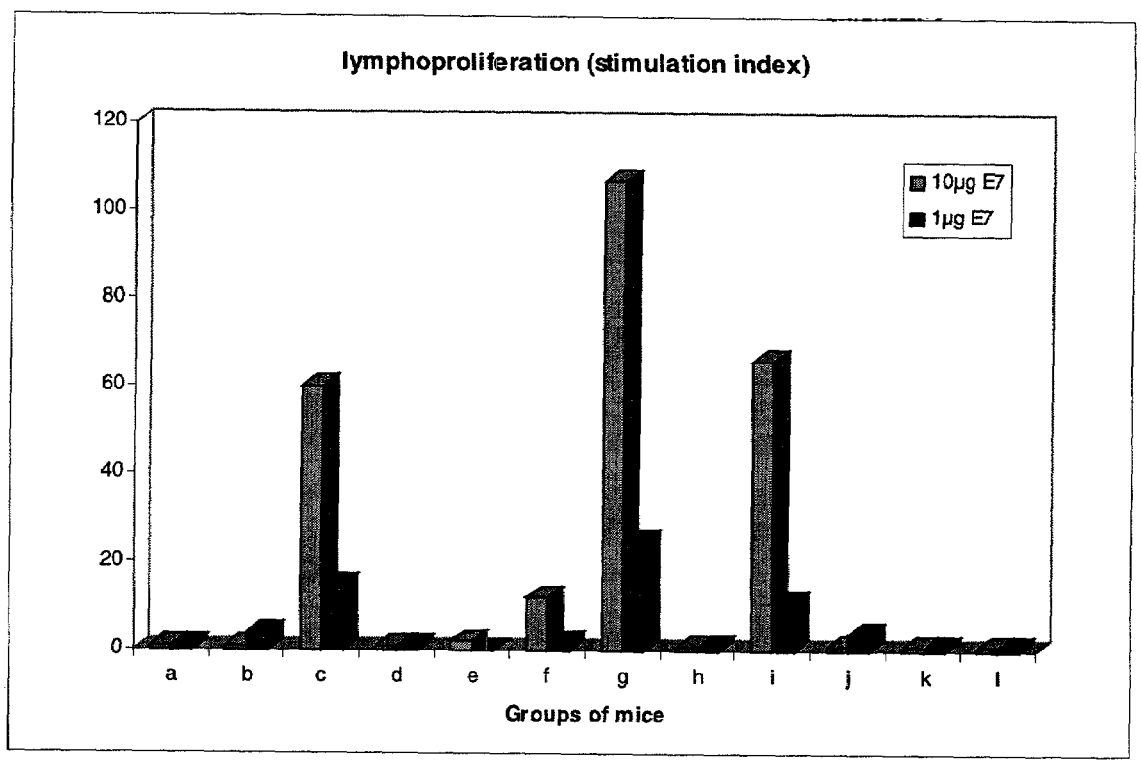
FIG. 18, Lymphoproliferation observed in spleen cells, 2 weeks after the second vaccination.
Figure 19:
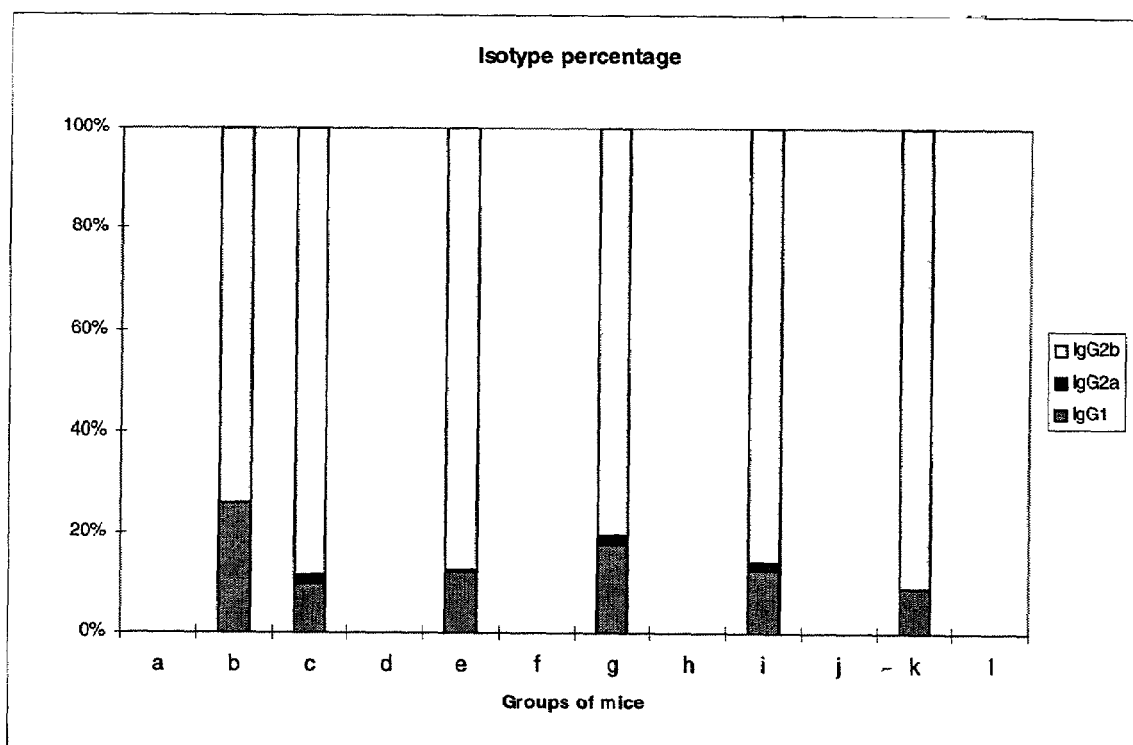
FIG. 19, Shows the relative percentage of the different IgG isotypes in the serum of vaccinated mice 2 weeks after the second vaccination.

Proliferation Results
   No proliferative response was observed in this experiment either with spleen or lymph node cells from mice that received ProtD⅓ E7 or adjuvants alone.
Antigen specific lymphoproliferation was increased in the groups of mice that received protD ⅓ E7 in the presence of adjuvants. High proliferative responses were observed with both DQ, and SB62' in the spleen. See FIGS. 17 and 18.
   FIG. 17, Lymphoproliferation observed in spleen cells, 2 weeks after the second vaccination.
   FIG. 18, Lymphoproliferation observed in spleen cells, 2 weeks after the second vaccination.
Serology
   Anti E7 antibody response: IgG total and sub-isotypes (IgG1, IgG2a, IgG2b ) were measured by ELISA using the E7 protein as coating antigen. The anti-E7 Ig titres observed 2 weeks after the second vaccination are given in table 6. FIG. 19, shows the relative percentage of the different IgG isotypes in the serum of vaccinated mice 2 weeks after the second vaccination
   The weak antibody response induced after 2 vaccinations with the ProtD⅓ E7 alone was strongly increased in animals in animals that received an adjuvant. The strongest antibody response was obtained with SB62.
   The predominant E7 specific antibody sub-isotype induced by all of the vaccine formulations tested was IgG2b (80-90% of the total IgGs).

TABLE 6 anti-E7 Ig titres observed 2 weeks after the second vaccination

| Group | Ig sub-isotype titre | | |
| --- | --- | --- | --- |
|  | IgG1 | IgG2a | IgG2b |
| a | 0 | 0 | 0 |
| b | 1420 | 0 | 4070 |
| c | 7850 | 1110 | 70170 |
| d | 0 | 0 | 0 |
| e | 11880 | 470 | 86610 |
| f | 0 | 0 | 0 |
| g | 13670 | 1580 | 62560 |
| h | 0 | 0 | 0 |
| i | 13073 | 1650 | 89930 |
| j | 0 | 0 | 0 |
| k | 260 | 0 | 2630 |
| l | 0 | 0 | 0 |

FIG. 19, Relative percentage of the different IgG isotypes in the serum of vaccinated mice 2 weeks after the second vaccination.
CTL Results
   A CTL response could be detected at time points 2 and 4 weeks after the final vaccination.
   No lysis was observed when mice received the protein or the adjuvant alone. The best specific lysis was observed when mice received the antigen in DQ or SB62' (see table 7).

TABLE 7

Summary of CTL responses after stimulation of splenic lymphocytes with TCL EL4+EL7

| Group | Anti-E7 CTL (E:T ratio 100:1) |
| --- | --- |
| a | − |
| b | − |
| c | +++ |
| d | − |
| e | ++ |
| f | − |
| g | ++++ |
| h | − |
| i | + |
| k | ++ |
| l | + |

Immunohistochemistry Results
   Tumors were removed from the mice (2 mice per group) and sections were frozen. Cryo section of tumors were stained with anti-CD4 and anti-CD8 antibodies. The results for the observed tumor infiltration by CD4 and CD8+ve cells are given in Table 8.

TABLE 8 results of lymphocytic tumour infiltration after vaccination with

| Group (Mouse No.) | Negative control | CD4+ve lymphocyte infiltration | CD8+ve lymphocyte infiltration |
| --- | --- | --- | --- |
| a(1) | − | − | +/− |
| a(2) | − | − | +/− |
| b(1) | − | +/− | + |
| b(2) | − | − | + |
| c(1) | − | + | +++ |
| c(2) | − | + | +++ |
| d(1) | − | − | +/− |
| d(2) | − | +/− | + |
| e(1) | − | +/− | +++ |
| e(2) | − | +/− | +++ |
| f(1) | − | − | +/− |
| f(2) | − | − | +/− |

Conclusions
   The regressing tumors, in the groups of mice that received the ProtD-⅓ E7 in DQ or SB62, showed a massive infiltration of with CD8+ cells and few CD4+ cells.
   Tumors removed from the animals that received the PBS, antigen, or adjuvants alone, did not contain any CD8+ve lymphocytic infiltration.
   Two vaccinations (on days 7, 14) with 5 µg ProtD ⅓ in different SB62 based formulations induced the rejection of pre-established E7 expressing tumors implanted at a distant site.
   Tumor rejection is associated with an anti E7 specific CTL response. There is a trend to have a slightly better CTL response in the individuals that rejected their tumors.
   Immunochemistry showed a massive infiltration of CD8+T cells in tumors that regressed upon vaccination with ProtD⅓ E7+DQ and SB62.
   Two vaccinations (on days 114 and 21 post tumour challenge) with 5 µg ProtD ⅓ E7 HPV16 in SB62 reduced the growth of these bigger tumors but do not induce complete regression.
   Four vaccinations (days 7, 14, 21, and 28 post tumour challenge) with 5 µg ProtD ⅓ E7 HPV16 in SB62 induced the complete rejection of the established tumors in 60% of the animals. 40% total rejection was observed after 2 vaccinations with the same adjuvant.

The use of the low dose SB62' adjuvant had no effect on the magnitude of the anti-E7 antibody titres, yet induced the highest level of splenic lymphocyte proliferation and anti-E7 CTL responses.

Overall Conclusions to the Invention:

It is clear from the examples above that the present invention encompasses an oil in water emulsion which preferentially induces a strong Th1-type immune responses, especially IFN-γ production. These formulations have been demonstrated to stimulate immune responses to a wide variety of antigens and therefore, it is envisaged that this present invention shall find utility in a wide variety of pathogens not limited to those found herein.

EXAMPLE 5

Stabilisation of QS21 by Addition of Cholesterol

It has previously been described that QS21-H is hydrolysis product of QS21, that is no longer active as adjuvant. It is formed by cleavage of the QS21 molecule by OH⁻ from the aqueous solution. This reaction occurs where the pH of the aqueous medium is above a value of 6.5, and is accelerated by higher temperature. The oil-in-water emulsions described in this patent application (for example SB62) are known to exhibit a stabilising effect such that the hydrolysis of QS21 into QS21-H is inhibited. Upon dilution of the oil in water emulsion in the presence of constant QS21, they lose this stabilising property and the QS21 degenerates into the inactive QS21-H form. Surprisingly, emulsions containing additional Cholesterol, who at 1/1 ratio do not show an improved QS21 stability, maintain the stabilising effect even at a ⅕ dilution.

QS21 and QS21-H are assayed directly into the emulsion. This is achieved by chemically derivatising the complete formulation, and by performing a selective extraction step that dissolves the QS21, but leaves most interfering matrix compounds behind. The assay is HPLC based, and the compounds are dansylated. The dansylation is performed by drying down a sample of the emulsion, and adding 100 μl of 3.5 mg Dansyl hydrazine/ml C/M 2/1 and 100 μl of 1:4 Acetic acid: C/M 2/1 in that order. The mixture is well vortexed and incubated at 60° C. for 2 hours. The reaction mixture is dried in the Speedvac. It is reconstituted in 500 ll 30% ACN μin H2O, and centrifugated twice at 14000 rpm for two minutes. The supernatants are then collected in an autosampler tube. A standard curve is obtained by preparing QS21 and QS21-H in a mixture that contains the same compounds as the emulsion under study.

The HPLC assay is ran on a Vydac 218TP54 5 μ particle size C18 RP column, 250*4.6 mm. Solvents are A:H20+0, 05% TFA(trifluoracetic acid) and B:Acetonitrile+0,05% TFA. The gradient is:

| Time (min) | % A | % B |
|---|---|---|
| 0 | 70 | 30 |
| 2 | 70 | 30 |
| 15 | 50 | 50 |
| 17 | 50 | 50 |
| 17.1 | 10 | 90 |
| 19 | 10 | 90 |
| 21 | 70 | 30 |
| 25 | 70 | 30 |

The Flow rate is 1 ml/min. Detection is in fluorescence, with excitation at 345 run and emission at 515 nm. 50 μl is injected of both the sample and the standards. The column heater is set to 37° C. for this separation. Peaks for QS21, QS21-iso and QS21-H are distinguished on the chromatogram.

A series of samples with the following composition were analysed:

| Composition | SB62 | SB62c | MPL | QS21 |
|---|---|---|---|---|
| SB62 | 250 μl | – | 50 μg | 50 μg |
| SB62' | 50 μl | – | 50 μg | 50 μg |
| SB62c | – | 250 μl | 50 μg | 50 μg |
| SB62'c | – | 50 μl | 50 μg | 50 μg |

Assay of QS21/QS21-H was performed after incubation of the samples at various time intervals and temperatures (4° C. and 37° C.). The data for 1 month at 37° C. in this model correlate well with stability of QS21 after prolonged storage at 4° C. (eg 2 years).

TABLE 9

HPLC QS21 assay: % of QS21-H generated over time

| Composition | 3 months (4° C.) | 6 months (4° C.) | 3 months (4° C.) + 7 days (37° C.) | 1 month (37° C.) |
|---|---|---|---|---|
| SB62 | 1% | 2% | 3% | 15% |
| S262' | 1% | 1% | 9% | 31% |
| SB62c | 2% | 2% | 3% | 17% |
| SB62'c | 2% | 2% | 3% | 21% |

This results shown in the table above shows clearly (both for 7 days and 1 m) the effect of adding a sterol, in this case cholesterol, to SB62' in maintaining the stability of QS21.

The invention claimed is:

1. A composition comprising squalene in water emulsion and a saponin and 3-O-deacylated monophosphoryl lipid A characterised in that the ratio of the squalene:saponin (w/w) is substantially 48:1.

2. A composition as claimed in claim 1, where the saponin is derived from QuilA.

3. A composition as claimed in claim 1, further comprising a sterol.

4. A composition as claimed in claim 3, where the sterol is cholesterol.

5. A composition as claimed in claim 1, further comprising one or more additional immunomodulators.

6. A composition as claimed in claim 3, further comprising one or more additional immunomodulators.

7. A composition as claimed in claim 5, wherein said immunomodulator is α-tocopherol.

8. A composition as claimed in claim 2, wherein the saponin is QS21, characterised in that the ratio of QS21: 3-O-deacylated monophosphoryl lipid A (w/w) is from 1:10 to 10:1.

9. A composition as claimed in claim 8, wherein the ratio of QS21: 3-O-deacylated monophosphoryl lipid A (wlw) is from 1:1 to 1:2.5.

10. A composition as claimed in claim 1 further comprising cholesterol, and wherein the saponin is QS21, characterised in that the ratio of QS21:cholesterol (w/w) is in the range of 1:1 to 1:20.

11. A vaccine composition comprising a composition as claimed in any one of claims 1, 5, 7, 8, or 9, further comprising an antigen or antigenic preparation.

12. A vaccine composition as claimed in claim 11, where the antigen or antigenic preparation is selected from a group consisting of antigens or antigenic preparations derived from: Human Immunodeficiency Virus; Herpes Simplex Virus type 1; Herpes Simplex Virus type 2; Human Cytomegalovirus; Hepatitis A, B, C or E; Respiratory Syncitial Virus, Human Papilloma Virus; Influenza Virus; *Salmonella; Neisseria; Borrelia; Chlamydia; Bordetella*; TB; EBV; Plasmodium and Toxoplasma.

13. A vaccine composition as claimed in claim 11, wherein the antigen or antigenic preparation is a combination of the Malaria antigens RTS,S and TRAP.

14. A vaccine composition as claimed in claim 11, where the antigen or antigenic preparation is a tumour or host antigen, or an immunogenic protein or peptide thereof.

15. A vaccine composition as claimed in claim 11 that invokes a cytolytic T-cell response in a mammal to the antigen or antigenic composition.

16. A vaccine composition as claimed in claim 11 that stimulates interferon-γ production in mammal to the antigen or antigenic preparation.

17. A method for manufacturing a vaccine as claimed in claim 11, comprising admixing an oil in water emulsion; QS2; cholesterol; 3D-MPL; α-tocopherol; and an antigen or antigenic preparation.

18. A method of treating an individual susceptible to or suffering from a disease comprising the step of administering a vaccine composition as claimed in claim 11.

19. A method of stabilising a saponin present in a composition of claim 1, comprising the addition of a sterol into the oil phase of said oil in water emulsion.

20. A method as claimed in claim 19, wherein the saponin is QS21.

21. A method as claimed in claims 19 or 20 wherein the sterol is cholesterol.

22. A composition as claimed in claim 1, where the saponin is QS21.

* * * * *